(12) United States Patent
Schreck et al.

(10) Patent No.: US 10,874,502 B2
(45) Date of Patent: Dec. 29, 2020

(54) STENT GRAFT

(71) Applicant: Endologix LLC, Irvine, CA (US)

(72) Inventors: Stefan Schreck, Fallbrook, CA (US); Daniel Hawkins, Coto De Caza, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 15/911,629

(22) Filed: Mar. 5, 2018

(65) Prior Publication Data

US 2018/0193131 A1    Jul. 12, 2018

Related U.S. Application Data

(60) Continuation of application No. 14/461,308, filed on Aug. 15, 2014, now Pat. No. 9,907,642, which is a
(Continued)

(51) Int. Cl.
*A61F 2/07* (2013.01)
*A61F 2/856* (2013.01)
(Continued)

(52) U.S. Cl.
CPC ............ *A61F 2/07* (2013.01); *A61F 2/856* (2013.01); *A61F 2/2412* (2013.01); *A61F 2/89* (2013.01);
(Continued)

(58) Field of Classification Search
None
See application file for complete search history.

(56) References Cited

U.S. PATENT DOCUMENTS

| 2,127,903 A | 8/1938 | Bowen |
| 2,437,542 A | 5/1944 | Krippendorf |

(Continued)

FOREIGN PATENT DOCUMENTS

| CA | 2220141 | 11/1996 |
| CA | 2133530 | 1/1999 |

(Continued)

OTHER PUBLICATIONS

US 6,413,270 B1, 07/2002, Thornton et al. (withdrawn)
(Continued)

*Primary Examiner* — Leslie Lopez
(74) *Attorney, Agent, or Firm* — Foley & Lardner LLP

(57) ABSTRACT

Some embodiments are directed to a stent graft comprising a first stent graft having a first and a second stent and a first and a second inner graft supported by the first stent, and an outer graft. The second inner graft can be spaced apart from the first inner graft so that a portion of the first stent is not covered by either the first inner graft or the second inner graft. A first and second portion of the outer graft can be attached to the first stent, the outer graft being unsupported by the stent between the first and second portions so as to form a fillable space between the outer graft, the first inner graft, and the second inner graft. Some embodiments further comprise a second stent graft deployable within the inside of the first stent graft to sealingly cover the uncovered portion of the first stent.

19 Claims, 24 Drawing Sheets

Related U.S. Application Data division of application No. 13/397,952, filed on Feb. 16, 2012, now Pat. No. 8,821,564, which is a continuation of application No. 12/844,266, filed on Jul. 27, 2010, now Pat. No. 8,118,856.

(60) Provisional application No. 61/228,938, filed on Jul. 27, 2009, provisional application No. 61/248,105, filed on Oct. 2, 2009.

(51) Int. Cl.
   *A61F 2/06* (2013.01)
   *A61F 2/24* (2006.01)
   *A61F 2/89* (2013.01)
   *A61F 2/90* (2013.01)

(52) U.S. Cl.
   CPC ............ *A61F 2/90* (2013.01); *A61F 2002/065* (2013.01); *A61F 2002/067* (2013.01); *A61F 2002/075* (2013.01); *A61F 2002/077* (2013.01); *A61F 2220/005* (2013.01); *A61F 2220/0075* (2013.01); *A61F 2250/0024* (2013.01)

(56) References Cited

U.S. PATENT DOCUMENTS

| | | | |
|---|---|---|---|
| 2,845,959 | A | 8/1958 | Sidebotham |
| 2,990,605 | A | 7/1961 | Demsyk |
| 3,029,819 | A | 4/1962 | Starks |
| 3,096,560 | A | 7/1963 | Liebig |
| 3,769,336 | A | 10/1973 | Lee, Jr. et al. |
| 3,805,301 | A | 4/1974 | Liebig |
| 3,983,083 | A | 9/1976 | Kaetsu et al. |
| 3,996,938 | A | 12/1976 | Clark, III |
| 4,362,156 | A | 12/1982 | Feller, Jr. et al. |
| 4,473,067 | A | 9/1984 | Schiff |
| 4,497,074 | A | 2/1985 | Ray et al. |
| 4,501,263 | A | 2/1985 | Harbuck |
| 4,503,568 | A | 3/1985 | Madras |
| 4,525,157 | A | 6/1985 | Vaillancourt |
| 4,562,596 | A | 1/1986 | Kornberg |
| 4,580,568 | A | 4/1986 | Gianturco |
| 4,590,068 | A | 5/1986 | Berthet et al. |
| 4,592,754 | A | 6/1986 | Gupte et al. |
| 4,617,932 | A | 10/1986 | Kornberg |
| 4,641,653 | A | 2/1987 | Rockey |
| 4,650,466 | A | 3/1987 | Luther |
| 4,756,307 | A | 7/1988 | Crownshield |
| 4,800,882 | A | 1/1989 | Gianturco |
| 4,816,028 | A | 3/1989 | Kapadia et al. |
| 4,840,940 | A | 6/1989 | Sottiurai |
| 4,856,516 | A | 8/1989 | Hillstead |
| 4,878,906 | A | 11/1989 | Lindemann et al. |
| 4,907,336 | A | 3/1990 | Gianturco |
| 4,922,905 | A | 5/1990 | Strecker |
| 4,950,068 | A | 8/1990 | Mizuta |
| 4,981,478 | A | 1/1991 | Evard et al. |
| 4,981,947 | A | 1/1991 | Tomagou et al. |
| 4,994,069 | A | 2/1991 | Ritchrt et al. |
| 4,994,071 | A | 2/1991 | MacGregor |
| 4,998,539 | A | 3/1991 | Delsanti |
| 5,015,232 | A | 5/1991 | Maglinte |
| 5,019,090 | A | 5/1991 | Pinchuk |
| 5,034,001 | A | 7/1991 | Garrison et al. |
| 5,035,706 | A | 7/1991 | Giantureo et al. |
| 5,041,093 | A | 8/1991 | Chu |
| 5,064,435 | A | 11/1991 | Porter |
| 5,078,726 | A | 1/1992 | Kreamer |
| 5,102,417 | A | 4/1992 | Palmaz |
| 5,104,399 | A | 4/1992 | Lazarus |
| 5,104,404 | A | 4/1992 | Wolff |
| 5,108,424 | A | 4/1992 | Hoffman, Jr. et al. |
| 5,116,349 | A | 5/1992 | Aranyi |
| 5,123,917 | A | 6/1992 | Lee |
| 5,133,732 | A | 7/1992 | Wiktor |
| 5,135,535 | A | 8/1992 | Kramer |
| 5,135,536 | A | 8/1992 | Hillstead |
| 5,145,620 | A | 9/1992 | Sakai et al. |
| 5,147,334 | A | 9/1992 | Moss |
| 5,156,619 | A | 10/1992 | Ehrenfeld |
| 5,156,620 | A | 10/1992 | Pigott |
| 5,178,634 | A | 1/1993 | Martinez |
| 5,197,976 | A | 3/1993 | Herweck et al. |
| 5,201,757 | A | 4/1993 | Heyn et al. |
| 5,207,960 | A | 5/1993 | Moret de Rocheprise |
| 5,211,658 | A | 5/1993 | Clouse |
| 5,246,452 | A | 9/1993 | Sinnott |
| 5,256,141 | A | 10/1993 | Gancheff et al. |
| 5,275,622 | A | 1/1994 | Lazarus et al. |
| 5,282,860 | A | 1/1994 | Matsuno et al. |
| 5,282,824 | A | 2/1994 | Gianturco |
| 5,304,200 | A | 4/1994 | Spaulding |
| 5,314,444 | A | 5/1994 | Gianturco |
| 5,314,472 | A | 5/1994 | Fontaine |
| 5,316,023 | A | 5/1994 | Palmaz et al. |
| 5,320,602 | A | 6/1994 | Karpeil |
| 5,330,500 | A | 7/1994 | Song |
| 5,330,528 | A | 7/1994 | Lazim |
| 5,338,298 | A | 8/1994 | McIntyre |
| 5,342,387 | A | 8/1994 | Summers |
| 5,354,308 | A | 10/1994 | Simon et al. |
| 5,360,443 | A | 11/1994 | Barone et al. |
| 5,366,504 | A | 11/1994 | Andersen et al. |
| 5,370,683 | A | 12/1994 | Fontaine |
| 5,370,691 | A | 12/1994 | Samson |
| 5,383,892 | A | 1/1995 | Cardon et al. |
| 5,387,235 | A | 2/1995 | Chuter |
| 5,397,355 | A | 3/1995 | Marin et al. |
| 5,405,377 | A | 4/1995 | Cragg |
| 5,415,664 | A | 5/1995 | Pinchuk |
| 5,423,886 | A | 6/1995 | Arru et al. |
| 5,425,765 | A | 6/1995 | Tiefenbrun et al. |
| 5,443,477 | A | 8/1995 | Marin et al. |
| 5,443,498 | A | 8/1995 | Fontaine |
| 5,443,500 | A | 8/1995 | Sigwart |
| 5,449,372 | A | 9/1995 | Schmaltz et al. |
| 5,458,575 | A | 10/1995 | Wang |
| 5,458,615 | A | 10/1995 | Klemm et al. |
| 5,462,530 | A | 10/1995 | Jang |
| 5,464,419 | A | 11/1995 | Glastra |
| 5,464,450 | A | 11/1995 | Buscemi et al. |
| 5,484,444 | A | 1/1996 | Braunschweiler et al. |
| 5,489,295 | A | 2/1996 | Piplani et al. |
| 5,496,365 | A | 3/1996 | Sgro |
| 5,507,767 | A | 4/1996 | Maeda et al. |
| 5,507,769 | A | 4/1996 | Marin et al. |
| 5,507,770 | A | 4/1996 | Turk |
| 5,507,771 | A | 4/1996 | Gianturco |
| 5,514,154 | A | 5/1996 | Lau et al. |
| 5,514,379 | A | 5/1996 | Weissleder et al. |
| 5,522,880 | A | 6/1996 | Barone et al. |
| 5,522,881 | A | 6/1996 | Lentz |
| 5,522,883 | A | 6/1996 | Slater et al. |
| 5,530,528 | A | 6/1996 | Houki et al. |
| 5,534,024 | A | 7/1996 | Rogers et al. |
| 5,545,211 | A | 8/1996 | An et al. |
| 5,545,118 | A | 9/1996 | Fang |
| 5,554,180 | A | 9/1996 | Turk |
| 5,554,181 | A | 9/1996 | Das |
| 5,562,697 | A | 10/1996 | Christiansen |
| 5,562,726 | A | 10/1996 | Chuter |
| 5,562,727 | A | 10/1996 | Turk et al. |
| 5,562,728 | A | 10/1996 | Lazarus et al. |
| 5,571,173 | A | 11/1996 | Parodi |
| 5,575,816 | A | 11/1996 | Rudnick et al. |
| 5,575,818 | A | 11/1996 | Pinchuk |
| 5,578,071 | A | 11/1996 | Parodi |
| 5,578,072 | A | 11/1996 | Barone et al. |
| 5,591,197 | A | 1/1997 | Orth et al. |
| 5,591,198 | A | 1/1997 | Boyle et al. |
| 5,591,199 | A | 1/1997 | Porter et al. |
| 5,591,229 | A | 1/1997 | Parodi |

(56) References Cited

U.S. PATENT DOCUMENTS

| | | |
|---|---|---|
| 5,591,230 A | 1/1997 | Horn et al. |
| 5,593,417 A | 1/1997 | Rhodes |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,312 A | 7/1997 | Fischell et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,968 A | 12/1997 | Rogers et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,725,535 A | 3/1998 | Hegde et al. |
| 5,733,303 A | 3/1998 | Israel et al. |
| 5,733,325 A | 3/1998 | Robinson et al. |
| 5,746,776 A | 5/1998 | Smith et al. |
| 5,749,880 A | 5/1998 | Banas et al. |
| 5,752,974 A | 5/1998 | Rhee et al. |
| 5,755,770 A | 5/1998 | Ravenscroft |
| 5,755,771 A | 5/1998 | Penn et al. |
| 5,755,777 A | 5/1998 | Chuter |
| 5,769,882 A | 6/1998 | Fogarty et al. |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,785,679 A | 7/1998 | Abolfathi et al. |
| 5,800,407 A | 9/1998 | Eldor |
| 5,800,456 A | 9/1998 | Maeda et al. |
| 5,800,508 A | 9/1998 | Goicoechea et al. |
| 5,800,526 A | 9/1998 | Anderson et al. |
| 5,810,836 A | 9/1998 | Hussein et al. |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,846,261 A | 12/1998 | Kotula et al. |
| 5,851,228 A | 12/1998 | Pinheiro |
| 5,855,565 A | 1/1999 | Bar-Cohen et al. |
| 5,855,599 A | 1/1999 | Wan |
| 5,860,998 A | 1/1999 | Robinson et al. |
| 5,867,432 A | 2/1999 | Toda |
| 5,868,783 A | 2/1999 | Tower |
| 5,871,536 A | 2/1999 | Lazarus |
| 5,871,537 A | 2/1999 | Holman et al. |
| 5,874,500 A | 2/1999 | Rhee et al. |
| 5,879,321 A | 3/1999 | Hill |
| 5,879,366 A | 3/1999 | Shaw et al. |
| 5,891,193 A | 4/1999 | Robinson et al. |
| 5,893,887 A | 4/1999 | Jayaraman |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicoceha et al. |
| 5,919,225 A | 7/1999 | Lau et al. |
| 5,925,075 A | 7/1999 | Myers et al. |
| 5,928,279 A | 7/1999 | Shannon et al. |
| 5,931,866 A | 8/1999 | Frantzen |
| 5,935,161 A | 8/1999 | Robinson et al. |
| 5,938,696 A | 8/1999 | Goicoechea et al. |
| 5,948,018 A | 9/1999 | Dereume et al. |
| 5,957,901 A | 9/1999 | Mottola et al. |
| 5,957,973 A | 9/1999 | Quiachon et al. |
| 5,961,546 A | 10/1999 | Robinson et al. |
| 5,961,548 A | 10/1999 | Shmulewitz |
| 5,980,552 A | 11/1999 | Pinchasik et al. |
| 6,001,125 A | 12/1999 | Golds et al. |
| 6,004,347 A | 12/1999 | McNamara et al. |
| 6,004,348 A | 12/1999 | Banas et al. |
| 6,007,575 A | 12/1999 | Samuels |
| 6,015,431 A | 1/2000 | Thornton et al. |
| 6,017,363 A | 1/2000 | Hojeibane |
| 6,022,359 A | 2/2000 | Frantzen |
| 6,027,779 A | 2/2000 | Campbell et al. |
| 6,027,811 A | 2/2000 | Campbell et al. |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,932 A | 4/2000 | Daniel et al. |
| 6,053,940 A | 4/2000 | Wijay |
| 6,063,113 A | 5/2000 | Kavteladze |
| 6,070,589 A | 6/2000 | Keith et al. |
| 6,074,398 A | 6/2000 | Leschinsky |
| 6,077,296 A | 6/2000 | Shokoohi et al. |
| 6,077,297 A | 6/2000 | Robinson et al. |
| 6,083,259 A | 7/2000 | Frantzen |

(56) References Cited

U.S. PATENT DOCUMENTS

| | | | |
|---|---|---|---|
| 6,086,611 A | 7/2000 | Duffy et al. |
| 6,090,128 A | 7/2000 | Douglas |
| 6,093,203 A | 7/2000 | Uflacker |
| 6,096,053 A | 8/2000 | Bates |
| 6,106,548 A | 8/2000 | Reubin et al. |
| 6,117,167 A | 9/2000 | Goicoechea et al. |
| 6,123,715 A | 9/2000 | Amplatz |
| 6,123,722 A | 9/2000 | Fogarty et al. |
| 6,123,723 A | 9/2000 | Konya et al. |
| 6,124,523 A | 9/2000 | Banas et al. |
| 6,126,685 A | 10/2000 | Lenker et al. |
| 6,129,756 A | 10/2000 | Kugler et al. |
| 6,139,573 A | 10/2000 | Sogard et al. |
| 6,152,943 A | 11/2000 | Sawhney |
| 6,152,957 A | 11/2000 | Jang |
| 6,165,201 A | 12/2000 | Sawhney et al. |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,034 B1 | 2/2001 | Frantzen |
| 6,187,036 B1 | 2/2001 | Shaolian |
| 6,192,944 B1 | 2/2001 | Greenhalgh |
| 6,197,049 B1 | 3/2001 | Shaolian et al. |
| 6,203,735 B1 | 3/2001 | Edwin et al. |
| 6,214,022 B1 | 4/2001 | Taylor et al. |
| 6,221,102 B1 | 4/2001 | Baker et al. |
| 6,231,562 B1 | 5/2001 | Khosravi et al. |
| 6,231,563 B1 | 5/2001 | White et al. |
| 6,245,099 B1 | 6/2001 | Edwin et al. |
| 6,261,316 B1 | 7/2001 | Shaolian et al. |
| 6,267,775 B1 | 7/2001 | Clerc et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,299,597 B1 | 10/2001 | Buscemi et al. |
| 6,312,407 B1 | 11/2001 | Zadno-Azizi et al. |
| 6,312,462 B1 | 11/2001 | McDermott et al. |
| 6,325,819 B1 | 12/2001 | Pavcnik et al. |
| 6,344,053 B1 | 2/2002 | Boneau |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,557 B1 | 3/2002 | Gittings et al. |
| 6,361,637 B2 | 3/2002 | Martin et al. |
| 6,375,666 B1 | 4/2002 | Mische |
| 6,375,675 B2 | 4/2002 | Dehdashtian et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,413,273 B1 | 7/2002 | Baum et al. |
| 6,416,474 B1 | 7/2002 | Penner et al. |
| 6,416,542 B1 | 7/2002 | Marcade et al. |
| 6,432,131 B1 | 8/2002 | Ravenscroft |
| 6,432,134 B1 | 8/2002 | Anson et al. |
| 6,436,135 B1 | 8/2002 | Goldfarb |
| 6,440,171 B1 | 8/2002 | Doubler et al. |
| 6,464,721 B1 | 10/2002 | Marcade et al. |
| 6,475,166 B1 | 11/2002 | Escano |
| 6,475,170 B1 | 11/2002 | Doron et al. |
| 6,491,719 B1 | 12/2002 | Fogrty et al. |
| 6,500,202 B1 | 12/2002 | Shaolian et al. |
| 6,508,833 B2 | 1/2003 | Pavcnick et al. |
| 6,508,835 B1 | 1/2003 | Shaolian et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,524,336 B1 * | 2/2003 | Papazolgou ............... A61F 2/07 623/1.16 |
| 6,533,763 B1 | 3/2003 | Schneiter |
| 6,533,811 B1 | 3/2003 | Ryan et al. |
| 6,551,350 B1 | 4/2003 | Thornton et al. |
| 6,558,396 B1 | 5/2003 | Inoue |
| 6,558,414 B2 | 5/2003 | Layne |
| 6,562,063 B1 | 5/2003 | Euteneurer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,576,009 B2 | 6/2003 | Ryan et al. |
| 6,582,460 B1 | 6/2003 | Cryer |
| 6,585,758 B1 | 7/2003 | Chouinard et al. |
| 6,592,614 B2 | 7/2003 | Lenker et al. |
| 6,592,615 B1 | 7/2003 | Marcade et al. |
| 6,605,294 B2 | 8/2003 | Sawhney |
| 6,610,087 B1 | 8/2003 | Zarbatany et al. |
| 6,613,073 B1 | 9/2003 | White et al. |
| 6,614,026 B1 | 9/2003 | Adamec |
| 6,616,675 B1 | 9/2003 | Evard et al. |
| 6,626,939 B1 | 9/2003 | Burnside et al. |
| 6,638,468 B1 | 10/2003 | Hill et al. |
| 6,652,579 B1 | 11/2003 | Cox et al. |
| 6,669,718 B2 | 12/2003 | Besselink |
| 6,673,042 B1 | 1/2004 | Samson et al. |
| 6,673,105 B1 | 1/2004 | Chen |
| 6,689,157 B2 | 2/2004 | Madrid et al. |
| 6,692,512 B2 | 2/2004 | Jang |
| 6,695,833 B1 | 2/2004 | Frantzen |
| 6,695,875 B2 | 2/2004 | Stelter et al. |
| 6,699,276 B2 | 3/2004 | Sogard et al. |
| 6,706,064 B1 | 3/2004 | Anson |
| 6,719,797 B1 | 4/2004 | Ferree |
| 6,729,356 B1 | 5/2004 | Baker et al. |
| 6,730,119 B1 | 5/2004 | Smalling |
| 6,733,523 B2 | 5/2004 | Shaolian et al. |
| 6,748,953 B2 | 6/2004 | Sherry et al. |
| 6,756,007 B2 | 6/2004 | Pletzer et al. |
| 6,761,733 B2 | 7/2004 | Chobotov et al. |
| 6,767,359 B2 | 7/2004 | Weadock |
| 6,770,091 B2 | 8/2004 | Richter et al. |
| 6,818,014 B2 | 11/2004 | Brown et al. |
| 6,818,018 B1 | 11/2004 | Sawhney |
| 6,821,292 B2 | 11/2004 | Pazienza et al. |
| 6,858,037 B2 | 2/2005 | Penn et al. |
| 6,899,728 B1 | 5/2005 | Phillips et al. |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,953,475 B2 | 10/2005 | Shaolian et al. |
| 6,960,217 B2 | 11/2005 | Bolduc |
| 6,969,373 B2 | 11/2005 | Schwartz et al. |
| 6,981,982 B2 | 1/2006 | Armstrong et al. |
| 6,984,244 B2 | 1/2006 | Perez et al. |
| 6,994,722 B2 | 2/2006 | DiCarlo |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,494 B2 | 4/2006 | Soun et al. |
| 7,029,496 B2 | 4/2006 | Rakos et al. |
| 7,033,389 B2 | 4/2006 | Sherry |
| 7,063,707 B2 | 6/2006 | Bose et al. |
| 7,074,213 B2 | 7/2006 | McGuckin, Jr. et al. |
| 7,074,236 B2 | 7/2006 | Rabkin et al. |
| 7,094,255 B2 | 8/2006 | Penn et al. |
| 7,108,715 B2 | 9/2006 | Lawrence-Brown et al. |
| 7,122,051 B1 | 10/2006 | Dallara et al. |
| 7,122,052 B2 | 10/2006 | Greenhalgh |
| 7,125,464 B2 | 10/2006 | Chobotov et al. |

(56) References Cited

U.S. PATENT DOCUMENTS

| | | |
|---|---|---|
| 7,147,660 B2 | 12/2006 | Chobotov et al. |
| 7,160,318 B2 | 1/2007 | Greenberg et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,192,441 B2 | 3/2007 | Sherry |
| 7,201,770 B2 | 4/2007 | Johnson et al. |
| 7,217,255 B2 | 5/2007 | Boyle et al. |
| 7,235,095 B2 | 6/2007 | Haverkost et al. |
| 7,241,308 B2 | 7/2007 | Andreas et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,314,483 B2 | 1/2008 | Landau et al. |
| 7,320,703 B2 | 1/2008 | DiMatteo et al. |
| 7,329,414 B2 | 2/2008 | Fisher et al. |
| 7,331,980 B2 | 2/2008 | Dubrul et al. |
| 7,347,850 B2 | 3/2008 | Sawhney |
| 7,402,168 B2 | 7/2008 | Acosta et al. |
| 7,435,253 B1 | 10/2008 | Hartley et al. |
| 7,476,232 B2 | 1/2009 | Deal |
| 7,491,230 B2 | 2/2009 | Holman et al. |
| 7,520,895 B2 | 4/2009 | Douglas et al. |
| 7,530,988 B2 | 5/2009 | Evans et al. |
| 7,553,324 B2 | 6/2009 | Andreas et al. |
| 7,572,289 B2 | 8/2009 | Sisken et al. |
| 7,588,825 B2 | 9/2009 | Bell et al. |
| 7,618,408 B2 | 11/2009 | Yandell |
| 7,623,909 B2 | 11/2009 | Sanghera et al. |
| 7,637,932 B2 | 12/2009 | Bolduc et al. |
| 7,651,519 B2 | 1/2010 | Dittman |
| 7,666,220 B2 | 2/2010 | Evans et al. |
| 7,666,333 B2 | 2/2010 | Lanphere et al. |
| 7,674,284 B2 | 3/2010 | Melsheimer |
| 7,682,383 B2 | 3/2010 | Robin |
| 7,691,135 B2 | 4/2010 | Shaolian et al. |
| 7,722,657 B2 | 5/2010 | Hartley |
| 7,727,228 B2 | 6/2010 | Abboud et al. |
| 7,766,959 B2 | 8/2010 | DiMatteo et al. |
| 7,790,273 B2 | 9/2010 | Lee et al. |
| 7,799,046 B2 | 9/2010 | White et al. |
| 7,803,178 B2 | 9/2010 | Whirley et al. |
| 7,833,259 B2 | 11/2010 | Boatman |
| 7,872,068 B2 | 1/2011 | Khosravi et al. |
| 7,879,081 B2 | 2/2011 | DeMatteo et al. |
| 7,897,086 B2 | 3/2011 | Khairkhahan et al. |
| 7,909,794 B2 | 3/2011 | Briscoe et al. |
| 7,910,129 B2 | 3/2011 | Kennedy et al. |
| 8,034,100 B2 | 10/2011 | Shaolian et al. |
| 8,118,856 B2 | 2/2012 | Schreck et al. |
| 8,216,295 B2 | 7/2012 | Benjamin et al. |
| 8,568,466 B2 | 10/2013 | Shaolian et al. |
| 8,821,564 B2 | 9/2014 | Schreck et al. |
| 2002/0049412 A1 | 4/2002 | Madrid et al. |
| 2002/0169497 A1 | 11/2002 | Wholey et al. |
| 2003/0004560 A1 | 1/2003 | Chobotov et al. |
| 2003/0014075 A1 | 1/2003 | Rosenbluth et al. |
| 2003/0051735 A1 | 3/2003 | Pavcnik et al. |
| 2003/0097169 A1 | 5/2003 | Brucker et al. |
| 2003/0194505 A1 | 10/2003 | Milbocker |
| 2003/0223957 A1 | 12/2003 | Schwartz et al. |
| 2003/0225453 A1 | 12/2003 | Murch |
| 2004/0016997 A1 | 1/2004 | Ushio |
| 2004/0098096 A1* | 5/2004 | Eton .......... A61F 2/07 623/1.13 |
| 2004/0116997 A1 | 6/2004 | Taylor et al. |
| 2004/0167597 A1 | 8/2004 | Costantino et al. |
| 2004/0167618 A1 | 8/2004 | Shaolian et al. |
| 2004/0176832 A1 | 9/2004 | Hartley et al. |
| 2004/0186471 A1 | 9/2004 | Trieu |
| 2004/0193245 A1 | 9/2004 | Deem et al. |
| 2004/0215322 A1 | 10/2004 | Kerr |
| 2005/0004660 A1 | 1/2005 | Rosenbluth et al. |
| 2005/0027238 A1 | 2/2005 | Fago et al. |
| 2005/0038494 A1 | 2/2005 | Eidenschink |
| 2005/0058327 A1 | 3/2005 | Pieper |
| 2005/0059994 A1 | 3/2005 | Walak et al. |
| 2005/0060025 A1 | 3/2005 | Mackiewicz et al. |
| 2005/0080476 A1 | 4/2005 | Gunderson et al. |
| 2005/0090804 A1 | 4/2005 | Chobotov et al. |
| 2005/0113693 A1 | 5/2005 | Smith et al. |
| 2005/0113905 A1 | 5/2005 | Greenberg et al. |
| 2005/0119731 A1 | 6/2005 | Brucker et al. |
| 2005/0121120 A1 | 6/2005 | Van Dijk et al. |
| 2005/0155608 A1 | 7/2005 | Pavcnik et al. |
| 2005/0158272 A1 | 7/2005 | Whirley et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0203206 A1 | 9/2005 | Trieu |
| 2005/0216047 A1 | 9/2005 | Kumoyama et al. |
| 2005/0220848 A1 | 10/2005 | Bates |
| 2005/0228480 A1 | 10/2005 | Douglas et al. |
| 2005/0240153 A1 | 10/2005 | Opie |
| 2005/0240258 A1 | 10/2005 | Bolduc et al. |
| 2005/0240260 A1 | 10/2005 | Bolduc |
| 2005/0271727 A1 | 12/2005 | Yao |
| 2006/0030911 A1 | 2/2006 | Letort |
| 2006/0074481 A1 | 4/2006 | Vardi et al. |
| 2006/0167538 A1 | 7/2006 | Rucker |
| 2006/0210635 A1 | 9/2006 | Laurent et al. |
| 2006/0212112 A1 | 9/2006 | Evans et al. |
| 2006/0233990 A1 | 10/2006 | Humphrey et al. |
| 2006/0233991 A1 | 10/2006 | Humphrey et al. |
| 2006/0292206 A1* | 12/2006 | Kim .......... A61B 17/12022 424/443 |
| 2007/0016243 A1 | 1/2007 | Ramaiah et al. |
| 2007/0027467 A1 | 2/2007 | Ortiz et al. |
| 2007/0050008 A1 | 3/2007 | Kim et al. |
| 2007/0055346 A1 | 3/2007 | Chu et al. |
| 2007/0142817 A1 | 6/2007 | Hurt |
| 2007/0150041 A1 | 6/2007 | Evans et al. |
| 2007/0156084 A1 | 7/2007 | Belhe et al. |
| 2007/0203571 A1 | 8/2007 | Kaplan et al. |
| 2007/0208367 A1 | 9/2007 | Fiorella et al. |
| 2007/0213804 A1 | 9/2007 | Schaeffer et al. |
| 2007/0213805 A1 | 9/2007 | Schaeffer et al. |
| 2007/0299497 A1 | 12/2007 | Shaolian et al. |
| 2008/0009936 A1 | 1/2008 | Kim et al. |
| 2008/0039923 A1 | 2/2008 | Taylor et al. |
| 2008/0132993 A1* | 6/2008 | Rasmussen .......... A61F 2/06 623/1.13 |
| 2008/0172122 A1 | 7/2008 | Mayberry et al. |
| 2008/0187591 A1 | 8/2008 | Rhee et al. |
| 2008/0188923 A1 | 8/2008 | Chu |
| 2008/0215087 A1 | 9/2008 | Pavcnik et al. |
| 2008/0228259 A1 | 9/2008 | Chu |
| 2008/0253987 A1 | 10/2008 | Rehor et al. |
| 2008/0275536 A1 | 11/2008 | Zarins et al. |
| 2008/0288044 A1 | 11/2008 | Osborne |
| 2008/0294237 A1 | 11/2008 | Chu |
| 2008/0300672 A1 | 12/2008 | Kassab et al. |
| 2009/0068279 A1 | 3/2009 | Richard |
| 2009/0081275 A1 | 3/2009 | Rolfes et al. |
| 2009/0112305 A1 | 4/2009 | Goldmann et al. |
| 2009/0117070 A1 | 5/2009 | Daniloff et al. |
| 2009/0117188 A1 | 5/2009 | Gershkovich et al. |
| 2009/0216315 A1 | 8/2009 | Schreck et al. |
| 2009/0238815 A1 | 9/2009 | Udipi et al. |
| 2009/0259298 A1 | 10/2009 | Mayberry et al. |
| 2009/0287145 A1 | 11/2009 | Cragg et al. |
| 2009/0294049 A1 | 12/2009 | Udipi et al. |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0004730 A1 | 1/2010 | Benjamin et al. |
| 2010/0036360 A1 | 2/2010 | Herbowy et al. |
| 2010/0094409 A1 | 4/2010 | Barker et al. |
| 2010/0100115 A1 | 4/2010 | Soetermans et al. |

(56) References Cited

U.S. PATENT DOCUMENTS

| | | | |
|---|---|---|---|
| 2011/0054586 A1 | 3/2011 | Mayberry et al. | |
| 2011/0054587 A1 | 3/2011 | Mayberry et al. | |
| 2011/0054594 A1 | 3/2011 | Mayberry et al. | |

FOREIGN PATENT DOCUMENTS

| | | |
|---|---|---|
| DE | 295 21 548 U1 | 2/1995 |
| DE | 295 21 776 U1 | 2/1995 |
| EP | 0 177 330 B1 | 6/1991 |
| EP | 0 596 145 A1 | 5/1994 |
| EP | 0 621 015 B1 | 10/1994 |
| EP | 0 659 389 A1 | 6/1995 |
| EP | 0 688 545 B1 | 12/1995 |
| EP | 0 689 806 A1 | 1/1996 |
| EP | 0 712 614 A1 | 5/1996 |
| EP | 0 732 088 A2 | 9/1996 |
| EP | 0 732 088 A3 | 9/1996 |
| EP | 0 740 928 A1 | 11/1996 |
| EP | 0 740 928 B1 | 11/1996 |
| EP | 0 747 020 A2 | 12/1996 |
| EP | 0 775 470 A1 | 5/1997 |
| EP | 0 782 841 B1 | 7/1997 |
| EP | 0 783 873 A2 | 7/1997 |
| EP | 0 783 873 B1 | 7/1997 |
| EP | 0 783 874 A2 | 7/1997 |
| EP | 0 783 874 B1 | 7/1997 |
| EP | 0 762 856 B1 | 9/1998 |
| EP | 0 880 948 A1 | 12/1998 |
| EP | 0 904 745 A2 | 3/1999 |
| EP | 0 974 314 A2 | 1/2000 |
| EP | 0 732 088 B1 | 4/2000 |
| EP | 1 054 648 B1 | 11/2000 |
| EP | 0 846 450 B1 | 12/2001 |
| EP | 0 846 449 B1 | 1/2002 |
| EP | 0 846 452 B1 | 1/2002 |
| EP | 1 214 020 B1 | 6/2002 |
| EP | 1 433 438 | 6/2004 |
| EP | 1 181 901 B1 | 11/2005 |
| EP | 1 110 515 B1 | 3/2006 |
| EP | 0 828 461 B2 | 7/2006 |
| EP | 1 181 902 | 3/2009 |
| ES | 1 038 606 | 7/1998 |
| ES | 1038606 | 7/1998 |
| FR | 2 834 199 | 7/2003 |
| JP | 04-25755 | 1/1992 |
| JP | 08-336597 | 12/1996 |
| JP | 9-511160 | 11/1997 |
| JP | 2000-500047 | 1/2000 |
| JP | 2003-250907 | 9/2003 |
| WO | WO 93/13825 | 7/1993 |
| WO | WO 94/24961 | 11/1994 |
| WO | WO 95/21592 | 8/1995 |
| WO | WO 96/18427 | 6/1996 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/19652 | 6/1997 |
| WO | WO 97/26936 | 7/1997 |
| WO | WO 97/29716 | 8/1997 |
| WO | WO 97/033532 | 9/1997 |
| WO | WO 97/045072 | 12/1997 |
| WO | WO 98/02100 | 1/1998 |
| WO | WO 98/41167 | 9/1998 |
| WO | WO 98/53761 | 12/1998 |
| WO | WO 99/029262 | 6/1999 |
| WO | WO 99/44536 | 9/1999 |
| WO | WO 99/47077 | 9/1999 |
| WO | WO 99/58084 | 11/1999 |
| WO | WO 00/51522 | 9/2000 |
| WO | WO 01/66038 | 9/2001 |
| WO | WO 01/87184 | 11/2001 |
| WO | WO 01/93782 | 12/2001 |
| WO | WO 02/00139 | 1/2002 |
| WO | WO 02/102282 | 12/2002 |
| WO | WO 04/037116 | 5/2004 |
| WO | WO 04/045393 | 6/2004 |
| WO | WO 05/037076 | 4/2005 |
| WO | WO 07/000790 | 1/2007 |
| WO | WO-2008107885 A2 * | 9/2008 ............... A61F 2/07 |

OTHER PUBLICATIONS

European Extended & Supplemental Searth Report re EP App. No. 10806904.8, dated Nov. 13, 2012.

Harris, J. Milton et al., Poly (ethylene glycol) Chemistry and Biological Applications, ACS Symposium Series, American Chemical Society, Washington DC, Developed from a symposium sponsored by the Division of Polymer Chemistry, Inc., at the 213$^{th}$ National Meeting of the American Chemical Society, San Francisco, CA, Apr. 13-17, 1997, Chapter 1; 12 pages.

International Search Report and Written Opinion re PCT/US2010/043432, dated Apr. 22, 2011.

Menger, et al., "Quantitative analysis of neovascularization of different PTEE-implants," *European Journal of Cardiothoracic Surgery*, (1990) 4:191-196.

Final Office Action dated Nov. 3, 2016, from U.S. Appl. No. 14/461,308.

Final Office Action dated Oct. 27, 2015, from U.S. Appl. No. 14/461,308.

International Report on Patentability and Written Opinion for PCT/US2010/043432, dated Jan. 31, 2012, dated Feb. 9, 2012.

Non-final Office Action dated Apr. 16, 2015, from U.S. Appl. No. 14/461,308.

Non-final Office Action dated Apr. 21, 2016, from U.S. Appl. No. 14/461,308.

\* cited by examiner

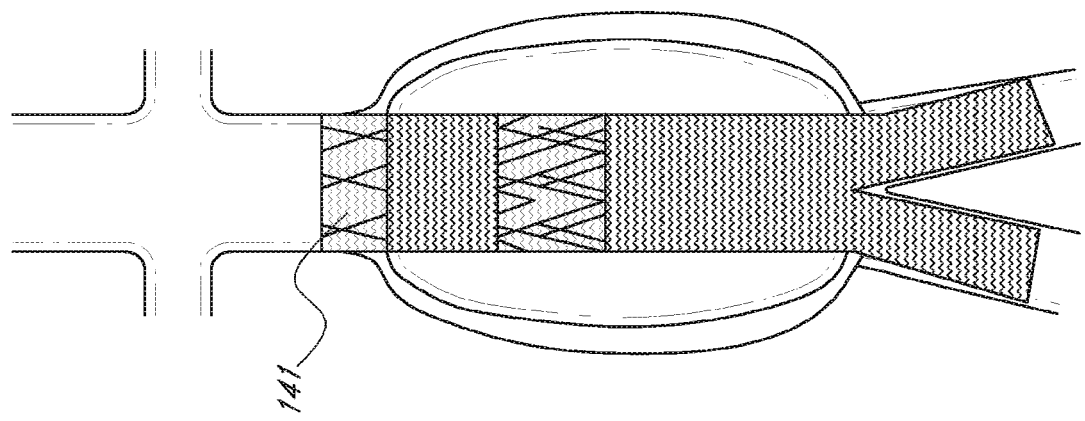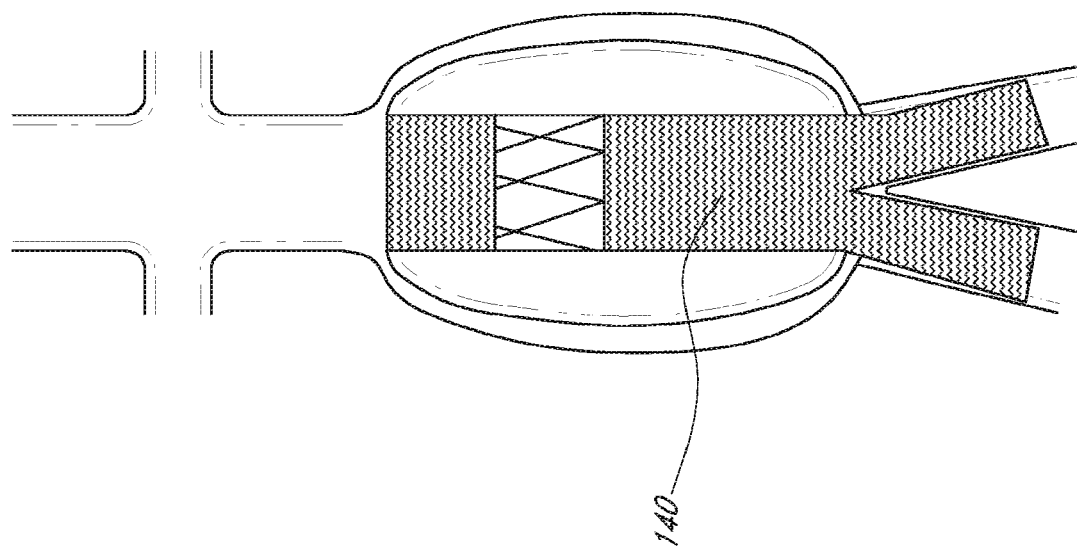
FIG. 19

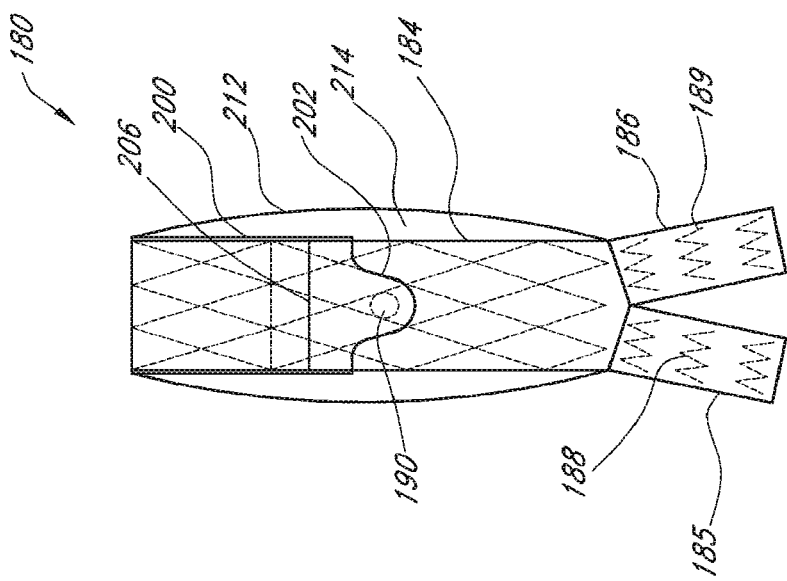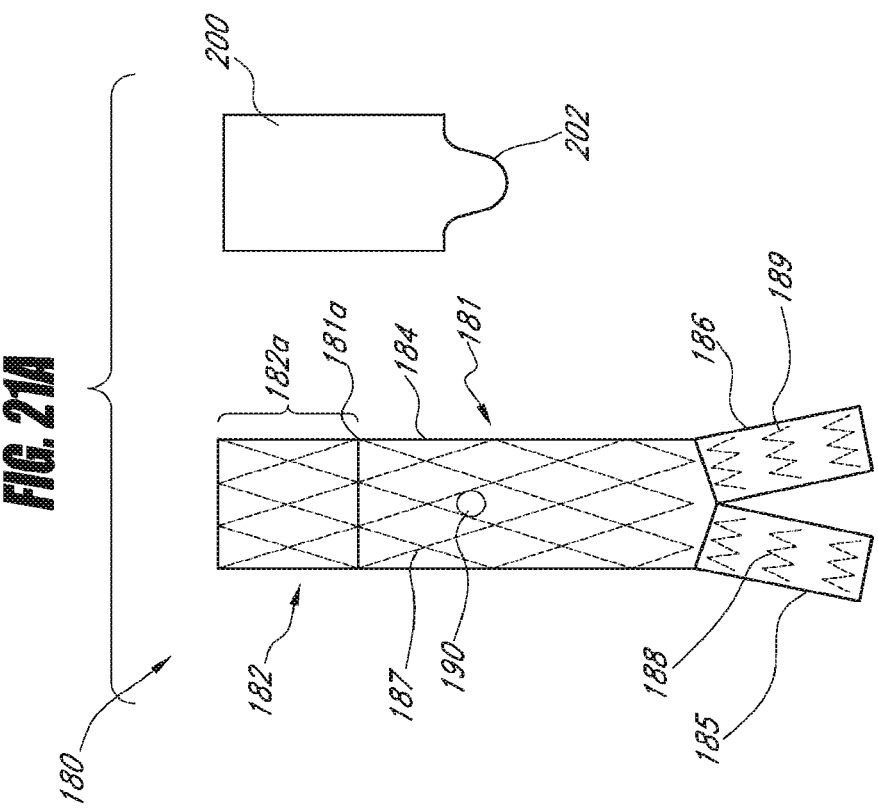

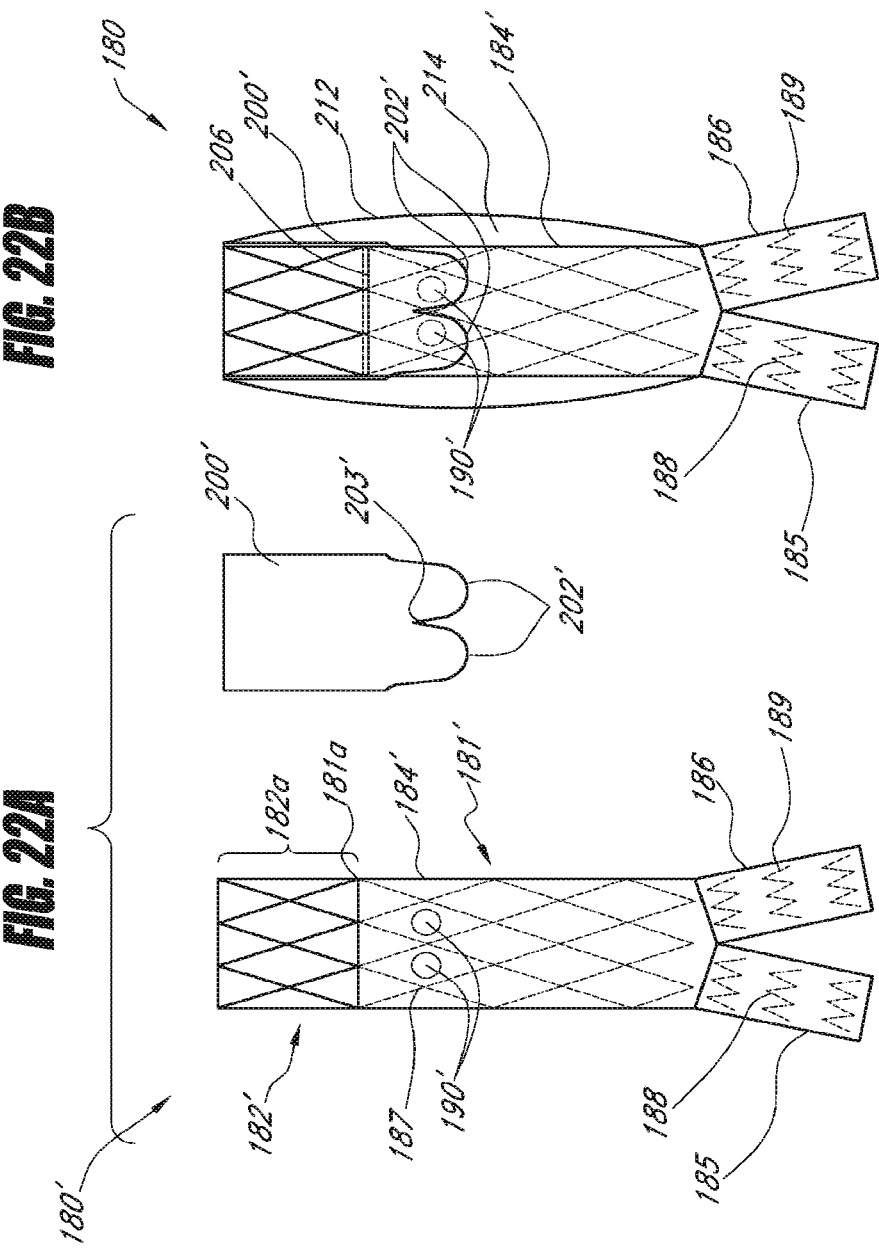

STENT GRAFT

PRIORITY INFORMATION AND INCORPORATION BY REFERENCE

This application is a continuation of U.S. patent application Ser. No. 14/461,308, filed on Aug. 15, 2014, which is a divisional of U.S. patent application Ser. No. 13/397,952, filed Feb. 16, 2012, now U.S. Pat. No. 8,821,564, which is a continuation of U.S. patent application Ser. No. 12/844,266, filed on Jul. 27, 2010, now U.S. Pat. No. 8,118,856, which claims priority benefit under 35 U.S.C. § 119(e) of U.S. Provisional Application No. 61/228,938, filed Jul. 27, 2009, and U.S. Provisional Application No. 61/248,105, filed Oct. 2, 2009, all of which applications are hereby incorporated by reference as if fully set forth herein.

BACKGROUND OF THE DISCLOSURE

Technical Field

The present disclosure relates to endoluminal vascular prostheses and methods of placing such prostheses, and, in one application, to endoluminal vascular prostheses for use in the treatment of Type II endoleaks.

Background

Stent grafts can be used for the endovascular treatment of aortic disease including aneurysms and dissections. The purpose of the stent graft is generally to isolate the diseased portion of the aortic wall from the aortic blood pressure and prevent further dilatation or rupture of the diseased portion of the aortic wall.

FIG. 1 shows an intrarenal abdominal aneurysm. The aorta 4 is enlarged below the renal arteries 2a, 2b and above the iliac arteries 3a, 3b. The enlarged aorta has formed an aneurysm sac 1. Pairs of lumbar arteries 5a, 5b branch from the aorta 4 in the region of the aneurysm sac 1.

FIG. 2 shows a bifurcated stent graft 10 placed in the aorta 4 to exclude the aneurysm sac 1 from the arterial blood pressure. The stent graft 10 creates a proximal seal distal to the renal arteries 2a, 2b and a distal seal 3a, 3b in the iliac arteries. An incomplete seal creates leakage flow from the aorta 4 into the aneurysm sac 1 and into the lumbar arteries 5a, 5b. A leak at the proximal or distal seal of the stent graft 10 is referred to as a Type I endoleak. A leak between overlapping components of the stent graft system 1 is referred to as a Type III endoleak. A leak through the covering of the stent graft is referred to as a Type IV endoleak. Type I, III, and IV are influenced by the specific design features of the stent graft 10.

There also exists a type of endoleak that is independent of the stent graft 10. The leak is created by pressure differences in the lumbar arteries 5a, 5b. FIG. 3 illustrates a leakage flow from a first pair of lumbar arteries 5a to a second pair of lumbar arteries 5b wherein the blood pressure in the first pair of lumbar arteries 5a is greater than that in the second pair of lumbar arteries 5b. This type of leak is referred to as Type II endoleak.

Current stent graft systems do not address the issue of Type II endoleaks. Type II endoleaks are present in a considerable number of patients after stent graft placement. These endoleaks can potentially cause continuing dilatation and even rupture of the aneurysm in some patients.

Various strategies have been developed to manage Type II endoleaks. In general, patients are monitored and their aneurysms are imaged routinely to ensure stabilization of the aneurysm. In case of persistent Type II endoleaks associated with aneurysm dilatation, interventions are recommended to embolize the endoleak. Coils or fast-curing polymers can be injected into the aneurismal sac to thrombose the blood in the sac and stop the blood flow between the lumbar arteries.

There is a clear need to manage Type II endoleaks. The current invention proposes a novel design of a stent graft that eliminates Type II endoleaks at the time of stent graft placement.

SUMMARY OF SOME EMBODIMENTS

Some embodiments described herein are directed to systems, methods and apparatuses for treating endovascular aneurysms or other endovascular defects such as Type II endoleaks (collectively referred to as "defects"). However, it will be appreciated that the systems, methods and apparatuses disclosed herein can be used in other fields or other portions of the body.

In some embodiments, such defects can be treated with a deployment system for deploying an endoluminal prosthesis within a passageway comprising a graft supported in a first position within a catheter and a stent supported in a second position within the catheter and configured to be expandable within the graft, wherein the first position does not overlap the second position. The stent can be self-expandable, balloon expandable, or expandable by other suitable means.

Some embodiments disclosed herein are directed to a stent graft system comprising a first stent graft having a first stent, a first inner graft supported by the first stent, a second inner graft supported by the first stent, and an outer graft. In some embodiments, the second inner graft can be spaced apart from the first inner graft so that a portion of the first stent is not covered by either the first inner graft or the second inner graft. A first portion and a second portion of the outer graft can be attached to the first stent, the outer graft being unsupported by the stent between the first and second portions so as to form a fillable space between the outer graft, the first inner graft, and the second inner graft. The stent graft system can further comprise a second stent graft deployable within the inside of the first stent graft so as to sealingly cover the uncovered portion of the first stent, the second stent graft having a second stent and a second graft and a length that is greater than a length of the uncovered portion of the first stent graft.

Some embodiments disclosed herein are directed to a stent graft system comprising a stent having a flow lumen therethrough, a first inner graft supported along at least a portion of the length of the stent, one or more openings formed through a wall of the first inner graft, one or more flap members configured to selectively cover the one or more openings formed through a wall of the first inner graft, and an outer graft positioned around the stent and configured to cover at least the one or more openings formed through the wall of the first inner graft. In some embodiments, the stent graft can be configured such that a substantially sealed space can be created between the outer graft and at least the first inner graft and the one or more flap members. The one or more flap members can be configured to permit blood to flow from the lumen through the openings into the space, and to at least inhibit the flow of blood from the space through the openings and into the lumen.

Some embodiments disclosed herein are directed to a method of treating a blood vessel with a stent graft, comprising positioning a first stent graft across the segment of the blood vessel to be treated, the first stent graft having a first stent, an inner graft having a first portion and a second portion, and an outer graft, filling the space between the inner graft and the outer graft through the uncovered portion of the stent with blood so that the outer graft expands outwardly away from the inner graft, and deploying a second stent graft inside the first stent graft so as to sealingly cover the uncovered portion of the first stent graft, the second stent graft having a second stent and a second graft. In some embodiments, the second portion of the inner graft can be spaced apart from the first portion of the inner graft so that a portion of the first stent can be uncovered by the inner graft, and a first portion and a second portion of the outer graft can be attached to at least one of the first stent and the inner graft. The outer graft can be unsupported by the first stent or inner graft between the first and second portions of the outer graft so as to create a fillable space between the outer graft and the inner graft.

Some embodiments disclosed herein are directed to a method of sealing a branch vessel with a stent graft, comprising positioning a first stent graft across the segment of the blood vessel to be treated, the first stent graft having a first stent, an inner graft having a first portion and a second portion, and an outer graft, filling the space between the inner graft and the outer graft through the uncovered portion of the stent with blood so that the outer graft expands outwardly away from the inner graft and covers an ostium to a branch vessel, and deploying a second stent graft inside the first stent graft so as to sealingly cover the uncovered portion of the first stent graft, the second stent graft having a second stent and a second graft. In some embodiments, the second portion of the inner graft can be spaced apart from the first portion of the inner graft so that a portion of the first stent is uncovered by the inner graft. Further, a first portion and a second portion of the outer graft can be attached to at least one of the first stent and the inner graft, the outer graft being unsupported by the first stent or inner graft between the first and second portions of the outer graft so as to create a fillable space between the outer graft and the inner graft.

Some embodiments disclosed herein are directed to a stent graft system comprising a stent, a first graft supported by the stent, and a second graft surrounding substantially all of an outside surface of the first graft. In some embodiments, the first graft is formed from a porous material and is sized to cover at least a portion of the length of the stent. A first portion and a second portion of the second graft can be attached to the first stent, the second graft being unsupported by the stent between the first and second portions so as to form a fillable space between the second graft and the first graft.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

FIG. 19 illustrates another embodiment of a two-layer graft system comprising a bifurcated stent graft having two graft layers and a second graft acting as a sealing member.

FIG. 21A illustrates some of the components of another embodiment of a stent graft system, showing the components in an unassembled state.

FIG. 21B illustrates the embodiment of the stent graft system of FIG. 21A, showing the components in the assembled state.

FIG. 22A illustrates some of the components of another embodiment of a stent graft system, showing the components in an unassembled state.

FIG. 22B illustrates the embodiment of the stent graft system of FIG. 22A, showing the components in the assembled state.

DETAILED DESCRIPTION OF SOME EXEMPLIFYING EMBODIMENTS

This disclosure sets forth various embodiments of a novel stent graft system and method to reduce or eliminate Type II endoleaks. The design can also be used to improve the seal of stent grafts in difficult anatomical situations. The following detailed description is now directed to certain specific embodiments of the disclosure. In this description, reference is made to the drawings wherein like parts are designated with like numerals throughout the description and the drawings.

Some embodiments described herein are directed to systems, methods, and apparatuses to treat Type II endoleaks, lesions, aneurysms, or other defects in the aorta, including, but not limited to, the thoracic, ascending, and abdominal aorta, to name a few. However, the systems, methods, and apparatuses may have application to other vessels or areas of the body, or to other fields, and such additional applications are intended to form a part of this disclosure. For example, it will be appreciated that the systems, methods, and apparatuses may have application to the treatment of blood vessels in animals. In short, the embodiments and/or aspects of the endoluminal prosthesis systems, methods, and apparatuses described herein can be applied to other parts of the body or may have other applications apart from the treatment of the thoracic, ascending, and abdominal aorta. And, while specific embodiments may be described herein with regard to particular portions of the aorta, it is to be understood that the embodiments described are adaptable for use in other portions of the aorta or other portions of the body and are not limited to the aortic portions described.

Figure 1:
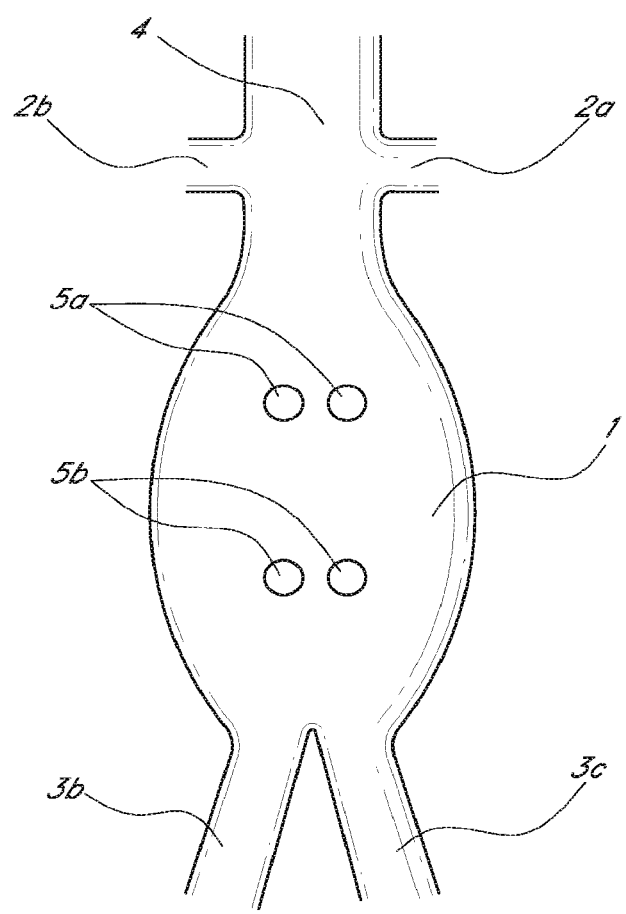
FIG. 1 illustrates an intrarenal abdominal aortic aneurysm.
Figure 2:
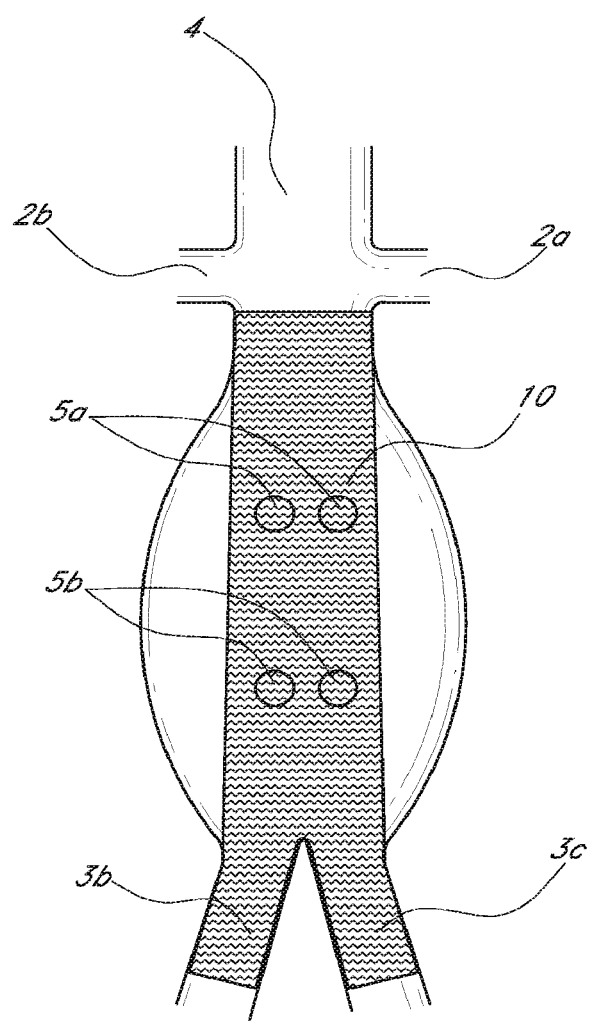
FIG. 2 illustrates a stent graft placed in the abdominal aneurysm.
Figure 3:
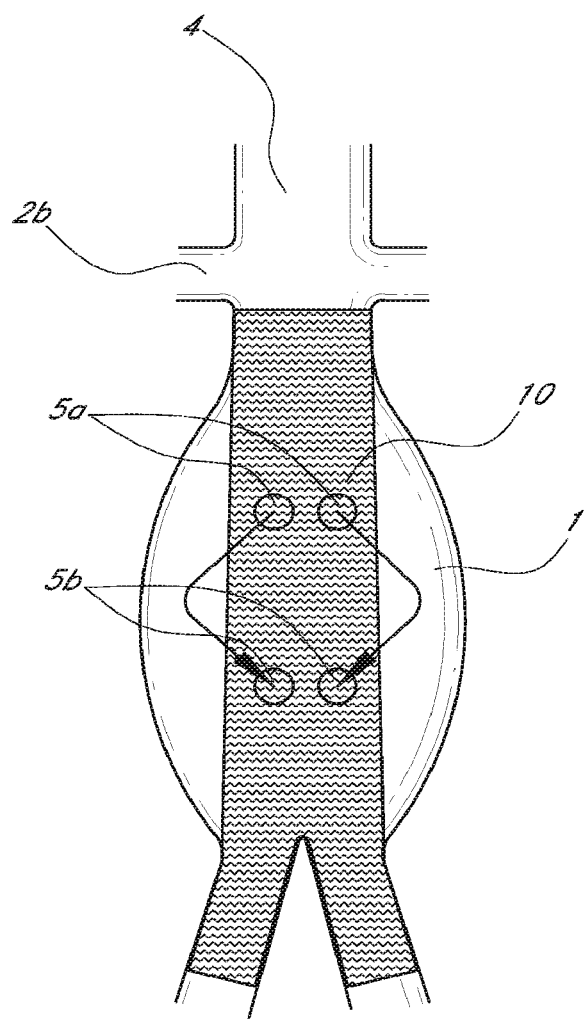
FIG. 3 illustrates type II endoleak after stent graft placement.

FIG. 1 illustrates an intrarenal abdominal aneurysm. The aorta 4 is enlarged below the renal arteries 2a, 2b and above the iliac arteries 3a, 3b. The enlarged aorta forms an aneurysm sac 1. Pairs of lumbar arteries 5a, 5b branch from the aorta 4 in the region of the aneurysm sac 1. FIG. 2 shows a bifurcated stent graft 10 placed in the aorta 4 to exclude the aneurysm sac 1 from the arterial blood pressure. FIG. 3 illustrates a leakage flow from a first pair of lumbar arteries 5a to a second pair of lumbar arteries 5b wherein the blood pressure in the first pair of lumbar arteries 5a is greater than that in the second pair of lumbar arteries 5b. This type of leak is referred to as Type II endoleak.

Figure 4A:
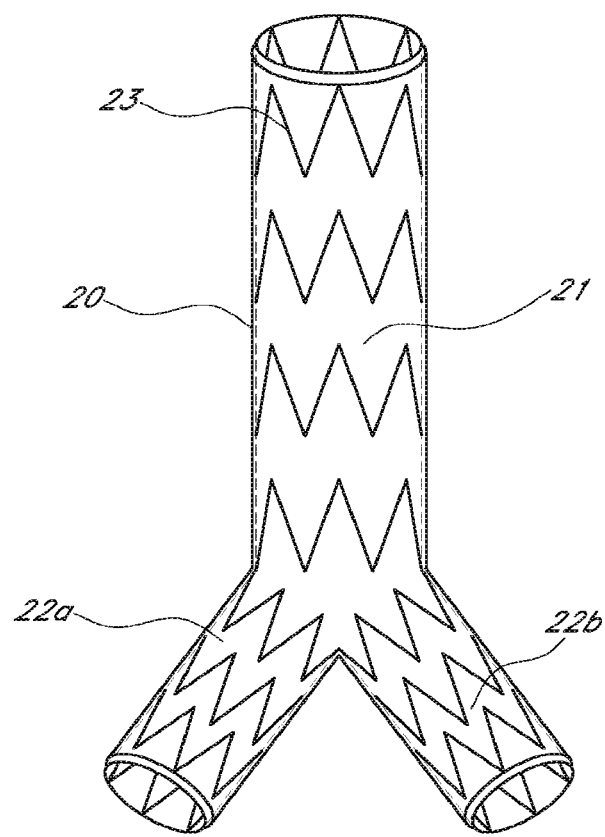
FIG. 4A illustrates an embodiment of a bifurcated stent graft used for the treatment of abdominal aortic aneurysms, wherein the graft is supported by stent segments.
Figure 4B:
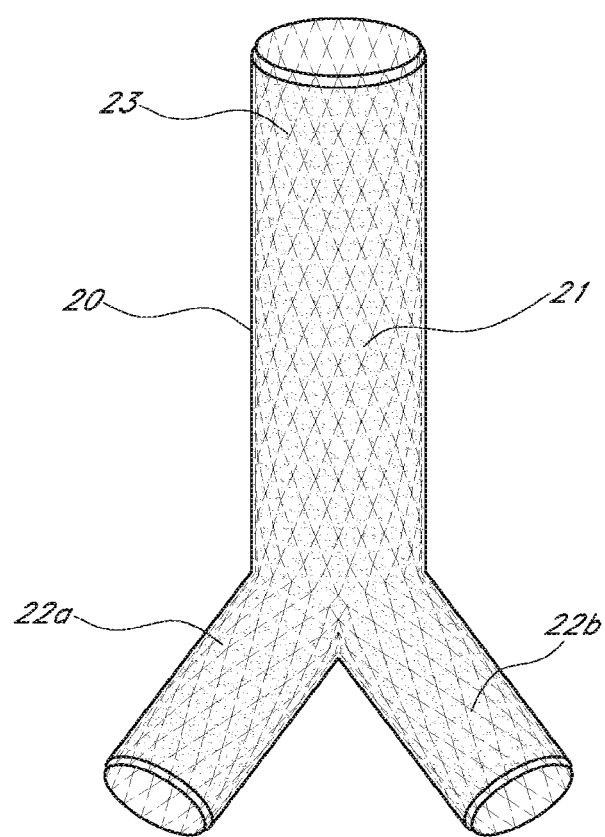
FIG. 4B illustrates an embodiment of a bifurcated stent graft used for the treatment of abdominal aortic aneurysms, wherein the graft is supported by a bifurcated stent.

FIG. 4 shows a typical stent graft 20 for the treatment of abdominal aortic aneurysms. The stent graft system can be a single piece bifurcated stent graft or a modular stent graft comprising two or more individual stent grafts that are assembled in situ. The stent graft 20 can consist of a main body 21 and two branch grafts 22a, 22b. The stent graft can have individual stent segments 23, as illustrated in FIG. 4A, or a bifurcated stent 24, as illustrated in FIG. 4B. The stent 24 or stent segments 23 can be self expandable, balloon expandable, or can be other similar or suitable stents. The graft 21 can be made from polyester, PTFE, ePTFE, or any other suitable material.

Figure 5:
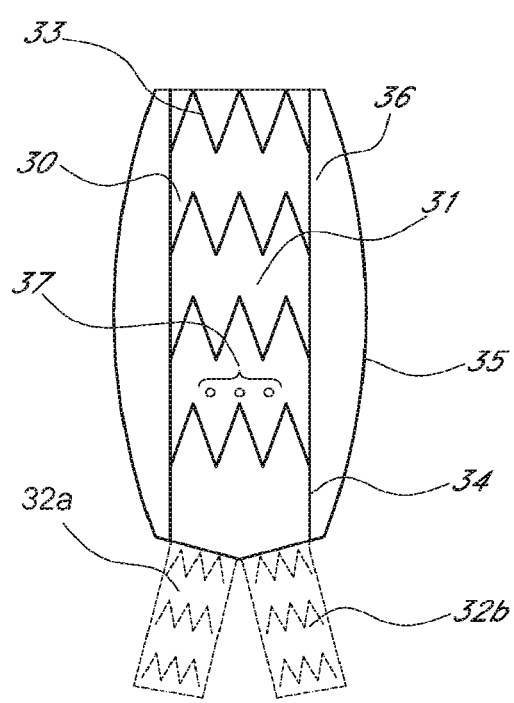
FIG. 5 illustrates an embodiment of a two-layer bifurcated stent graft used for the treatment of type II endoleaks.

FIG. 5 illustrates an embodiment of a two-layer bifurcated stent graft 30 used for the treatment of type II endoleaks. The basic construction of the stent graft 30 can be similar to that of any existing stent graft system having a main body 31, branch grafts 32a, 32b, stent segments 33, and a first inner graft cover 34. In some embodiments, the main body of the bifurcated stent graft can have a second, outer graft cover 35. The outer graft cover 35 can be made from the same material as the inner graft 34. In some embodiments, the outer graft cover 35, or any other outer graft embodiments disclosed herein, can have one or more radiopaque markers thereon to provide visualization of the position or level of inflation of the outer graft cover during deployment. Similarly, any of the stent or other graft embodiments disclosed herein can have one or more radiopaque markers thereon to provide visualization of the position of such prostheses during deployment.

The diameter of the outer graft cover 35 can be larger than that of the inner graft cover 34. In some embodiments, the outer graft cover 35 or any other outer graft cover embodiment disclosed herein can have a tubular shape, or can have a bulged middle portion such that the middle portion defines a greater diameter than the end portions of the outer graft cover 35. In some embodiments, the diameter of the outer graft cover 35 can be sufficiently large to expand to the flow lumen or against the inside surface of the aneurysm. The inner graft cover 34 and the outer graft cover 35 can be connected at the distal and proximal ends to form a sealed space 36. One or more openings 37, which can have any suitable size, large or small, can be cut or otherwise formed in the inner graft cover 34 to allow fluid communication between the inner lumen of the stent graft and the space 36.

In the embodiment described in FIG. 5, the opening in the inner graft layer can provide fluid communication between the inner lumen of the graft and the space between the inner graft layer and the outer graft layer. Preferably, the opening can be large enough to allow blood cells to enter the space. At the same time, the opening can be small enough to prevent flow patterns to form in the space that would delay blood coagulation. In some embodiments, the size of the opening can be between 20 μm and 5 mm. In some embodiments, the size of the opening can be between 100 μm and 2 mm. There can be one opening or multiple openings. The opening can be in form of holes punched into the graft material or in form of porous graft material (such as, without limitation, PTFE, ePTFE, polyester, or other suitable materials) with pore sizes sufficiently large to allow blood to enter the space between the inner and outer graft layer. Alternatively, the inner graft can be made from a porous metal. In some embodiments, a braided stent can form the inner graft. The gaps between the braids can allow blood to enter the space. The braided stent would eliminate the need for a separate stent to support the inner graft. The braided stent can be constructed from memory metals or memory plastics, or any other suitable material or materials.

Further, in some embodiments, the inner graft can be a generally non-porous material having a plurality of openings formed therein along at least a portion, or all of, the length of the inner graft layer. In some embodiments, as will be described in greater detail below, the inner graft layer can have pores or openings that are configured to allow one directional fluid flow. For example, the pores or openings can permit fluid to flow from an inside lumen through the inner graft, through the openings or pores in the inner graft layer, and into the space between the inner and outer graft layers, while being configured to prevent the flow of fluid (e.g., blood) from flowing in the opposite direction. Any of the embodiments of the graft layers disclosed herein, including the inner graft layer described above, can be used with any of the stent graft embodiments described in this application. For example, in some embodiments, the porous or perforated inner graft layer described herein can be used with any of the stent or stent graft embodiments disclosed herein with appropriate modifications, as necessary. All of such combinations are contemplated as forming a part of this disclosure.

In some embodiments, the inner graft material can be configured such that the pores or openings thrombose after a particular duration of exposure to a patient's blood. In this arrangement, the pores or openings in the inner graft material will essentially be sealed, so as to substantially inhibit or prevent the flow of blood through such openings or pores after the thrombosis of such openings or pores occurs. For example, the openings or pores can be configured to thrombose or become substantially sealed after the blood thinning agent (such as heparin) that is typically administered during arterial repair or other vascular procedures is removed or diminished from the patient's blood stream, thereby sealing the blood within the space between the inner and outer grafts within such space.

In some embodiments, the circumference of the outer graft cover can be larger than that of the inner graft. The outer graft cover can be large enough to inflate to the size of the flow lumen in the diseased blood vessel. In some embodiments, a substantial portion of the outer graft cover can touch the wall of the blood vessel when inflated. In the case of an abdominal aortic aneurysm, the diameter of the outer graft cover can be from approximately 4 cm or less to approximately 8 cm. In the case of an iliac aneurysm, the diameter of the outer graft can be from approximately 2 cm or less to approximately 4 cm. In some embodiments, the outer graft cover can be configured to only cover a portion of the inner graft cover. In some embodiments, the outer graft cover can be configured to only cover the distal portion, the proximal portion, or the mid-section of the inner graft cover. In some embodiments, the outer graft cover can be configured to only cover a portion of the circumference of the inner graft cover.

Figure 6:
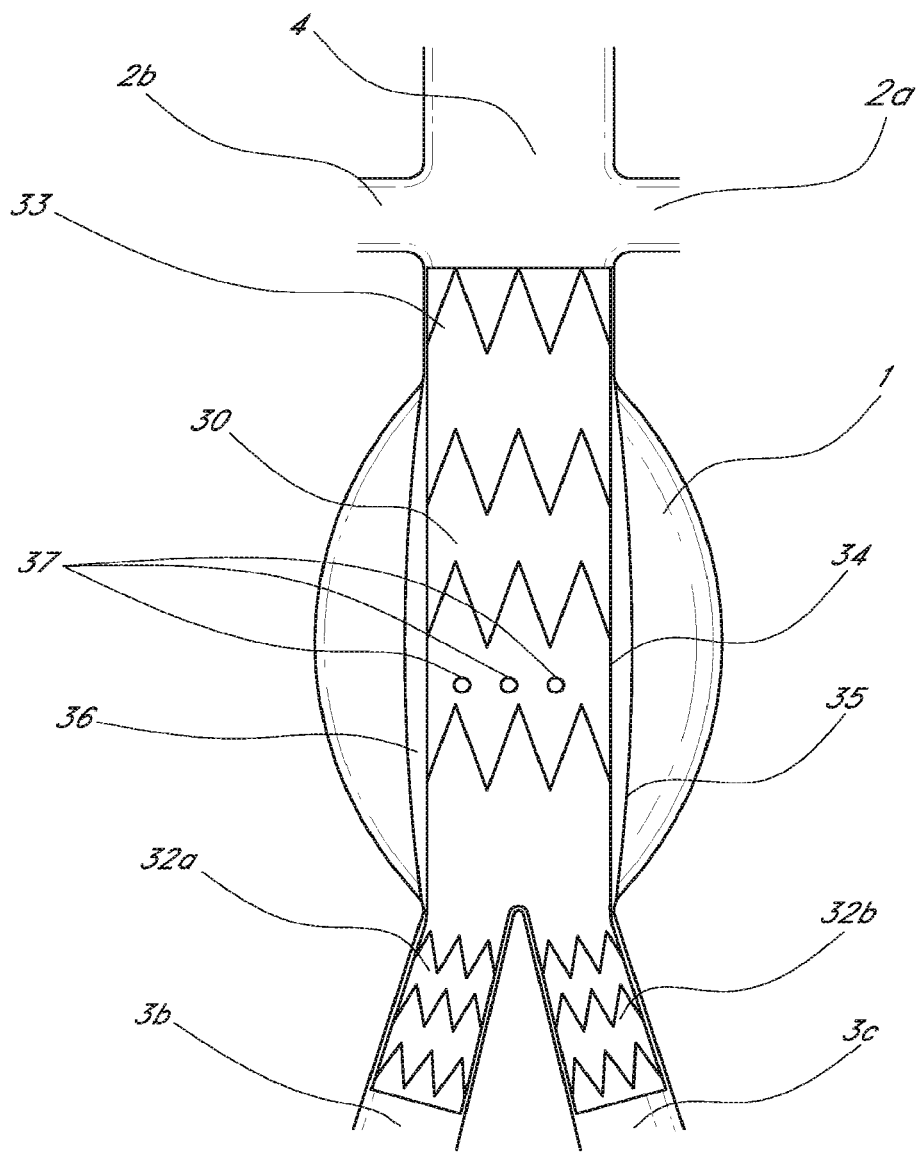
FIG. 6 illustrates the embodiment of the two-layer bifurcated stent graft illustrated in FIG. 5, placed in the abdominal aorta.

FIG. 6 illustrates the embodiment of the two-layer bifurcated stent graft 30 illustrated in FIG. 5, deployed in the abdominal aorta. The stent graft 30 can be positioned proximally below the renal arteries 2a and 2b and distally in the iliac arteries 3a and 3b. The stent graft 30 can seal the aneurysm 1 from the aorta 4. The inner graft cover 35 can form a flow lumen for blood through the aorta. The outer graft cover 36 can be initially collapsed onto the inner graft cover 35.

Figure 7:
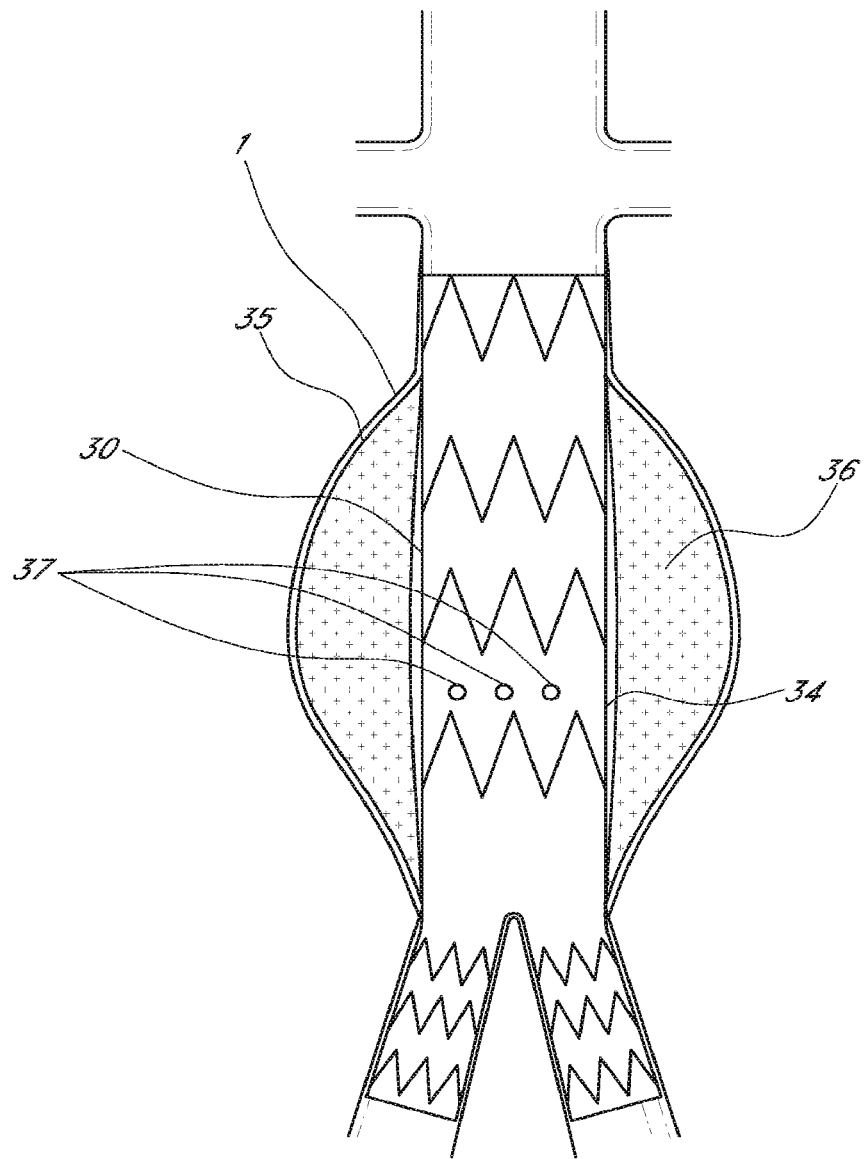
FIG. 7 illustrates the embodiment of the two-layer bifurcated stent graft illustrated in FIG. 5, with the space between the two layers of graft filled with blood.

FIG. 7 illustrates the embodiment of the two-layer bifurcated stent graft 30 illustrated in FIG. 5, with the space 36 between the two layers of graft filled with blood. As such, FIG. 7 shows the final configuration of the embodiment of the two-layer bifurcated stent graft 30 illustrated in FIG. 5. The blood in the aorta can enter through the openings 37 into the space 36 between the inner graft cover 34 and the outer graft cover 35. In some embodiments, the blood can cause the outer graft cover to inflate until it substantially fills or approximately completely fills the aneurysm sac. The blood in the space 36 can ultimately coagulate and form a thrombus.

Figure 8:
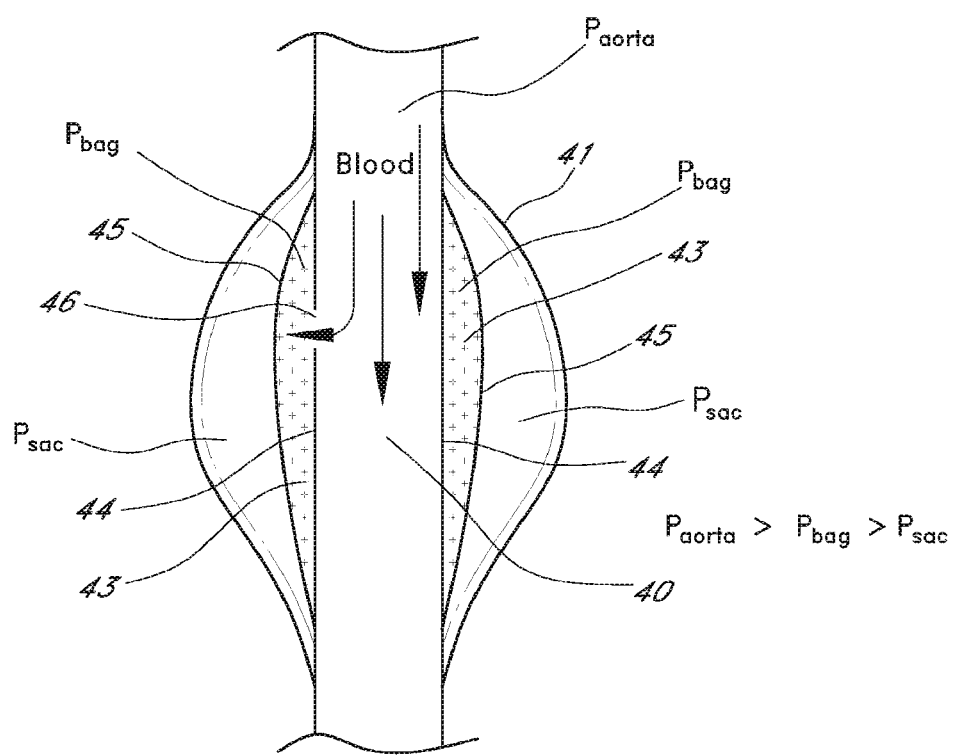
FIG. 8 illustrates the pressure distribution in the embodiment of the two-layer bifurcated stent graft illustrated in FIG. 5 after stent graft deployment.
Figure 9:
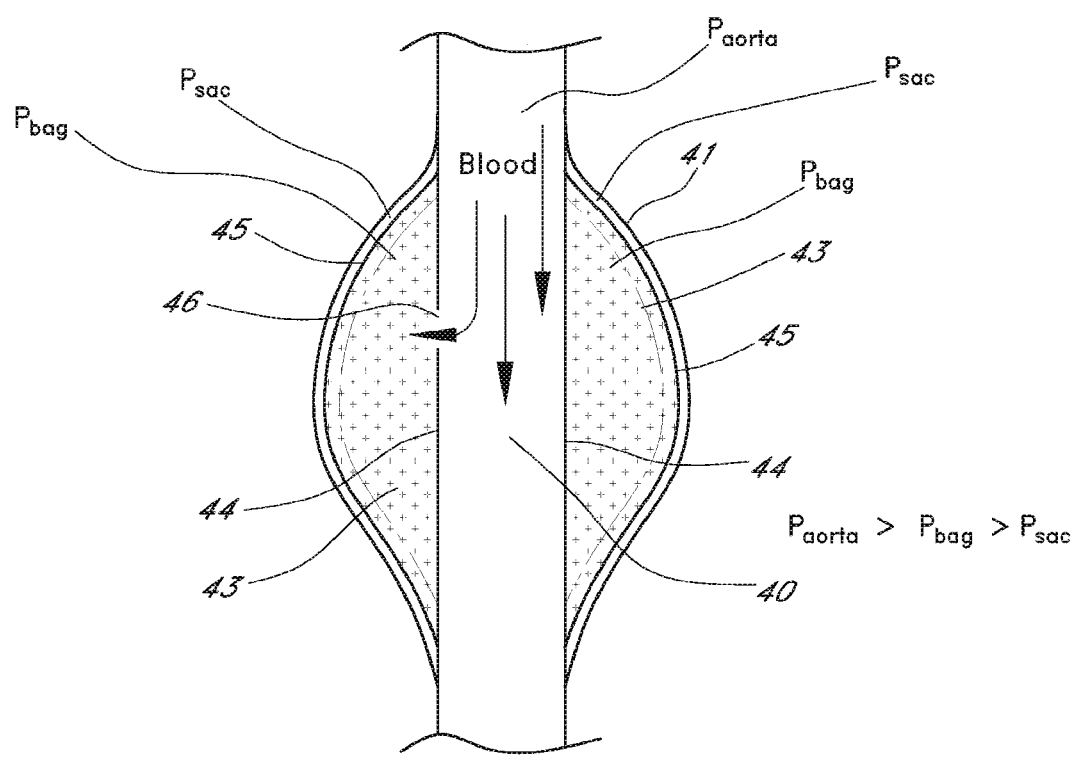
FIG. 9 illustrates the pressure distribution in the embodiment of the two-layer bifurcated stent graft illustrated in FIG. 5, after the space between the two layers of graft is filled with blood.

FIG. 8 illustrates the pressure distribution in the embodiment of the two-layer bifurcated stent graft 30 illustrated in FIG. 5 after stent graft deployment. FIG. 9 illustrates the pressure distribution in the embodiment of the two-layer bifurcated stent graft 30 illustrated in FIG. 5, after the space between the two layers of graft is filled with blood. As such, FIGS. 8 and 9 illustrate the mechanism of inflation or expansion of the outer graft cover. When the stent graft is placed in the abdominal aorta, the aneurysm 41 can be isolated from the aorta 40 as illustrated in FIG. 8. As a result, the pressure (Psac) in the aneurysm sac can drop. The pressure in the aorta (Paorta) is typically 60 mmHg-200 mmHg. The isolated aneurysm sac can be pressurized antegrade from the lumbar arteries. The pressure in the sac (Psac) is typically 30 mmHg-50 mmHg immediately after stent graft placement. After stent graft placement, the pressure in the aorta (Paorta) can push blood through the openings 46 into the space 43 between the inner graft cover 44 and the outer graft cover 45. The pressure in the space (Pbag) can rise above the sac pressure (Psac) and the outer graft 45 cover can inflate and expand approximately against the wall of the sac 41, displacing the blood in the sac 41. During the filling phase, the pressure in the space (Pbag) can be lower than the aortic pressure (Paorta) but higher than the sac pressure (Psac).

FIG. 9 illustrates the completed filling of the space 43. Once the outer graft cover 45 is fully inflated, the pressure in the space 43 can be approximately the same as the pressure in the aorta 41. Blood flow through the opening or openings 46 can thereafter be significantly reduced or can cease. The blood in the sac 41 can be completely displaced. The blood in the space 43 can be stagnant and can coagulate, forming thrombus. Once the thrombus is formed, the solid thrombus in the space 43 can isolate the pressure between the aorta and the aneurysm wall so that the aneurysm sac can be isolated from the aortic pressure.

Therefore, in some embodiments, a branch vessel adjacent to the outer graft layer 45 (for example, a lumbar or mesenteric artery) can facilitate the expansion of the outer graft layer against the inside surface of the vessel wall by reducing the pressure (Psac) within the space between the outer graft material and the vessel wall relative to the pressure within the aorta (Paorta). In this configuration, in some embodiments, the space 43 between the inner and outer layers can fill with blood from the aorta as the branch vessel reduces the pressure between the outer graft layer and the vessel wall, such that an additional instrument or medically administered injection of blood or fluid into (i.e., pressurization or inflation of) the space 43 may be avoided.

Type II endoleaks, as illustrated in FIG. 3, can be suppressed or eliminated by the expanded outer graft cover. The lumbar arteries 5a, 5b in FIG. 3 can be covered by the outer graft cover 45. Without limitation, one advantage of some embodiments of the proposed design is that the aneurysm sac can be filled and Type II endoleaks can be suppressed without the need for any additional procedural steps above and beyond the standard steps required to deploy a stent graft in the abdominal aorta. Furthermore, in some embodiments, no foreign material is needed to be introduced into the body or the prosthesis to embolize the sac.

The concept of a second outer graft layer can also be applied to the stent grafting of challenging anatomies in which is it difficult to obtain a seal between the graft and the vessel wall. For example, the blood vessel may have local calcium deposit, thrombus, or sudden changes in the diameter. The stent connected to the inner graft layer may not allow the inner graft to continuously contact the wall along the seal line. In the following disclosure, additional embodiments and examples are presented to illustrate further benefits of the second outer graft layer configuration.

Figure 10:
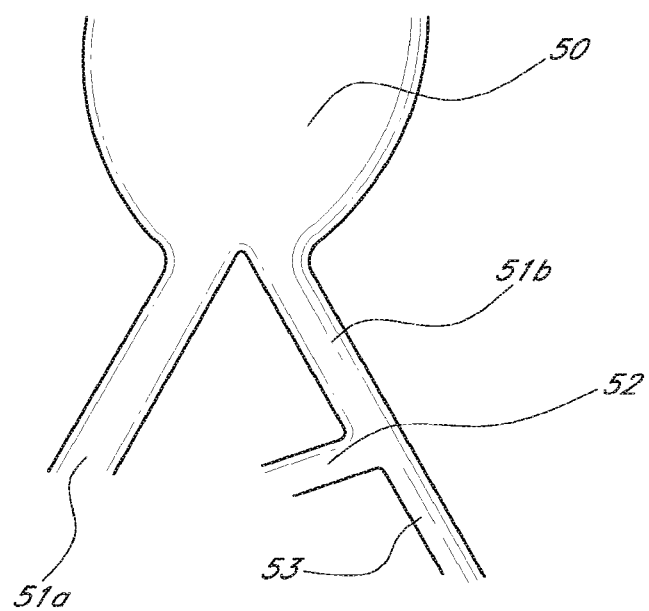
FIG. 10 illustrates a healthy common iliac and hypogastric artery in an abdominal aortic aneurysm.

FIG. 10 shows an abdominal aneurysm with the two common iliac arteries 51a and 51b branching from the aneurismal aorta 50. The common iliac artery 51a branches into the hypogastric artery 52 and the external iliac artery 53 about 3 cm-8 cm from the bifurcation.

Figure 11:
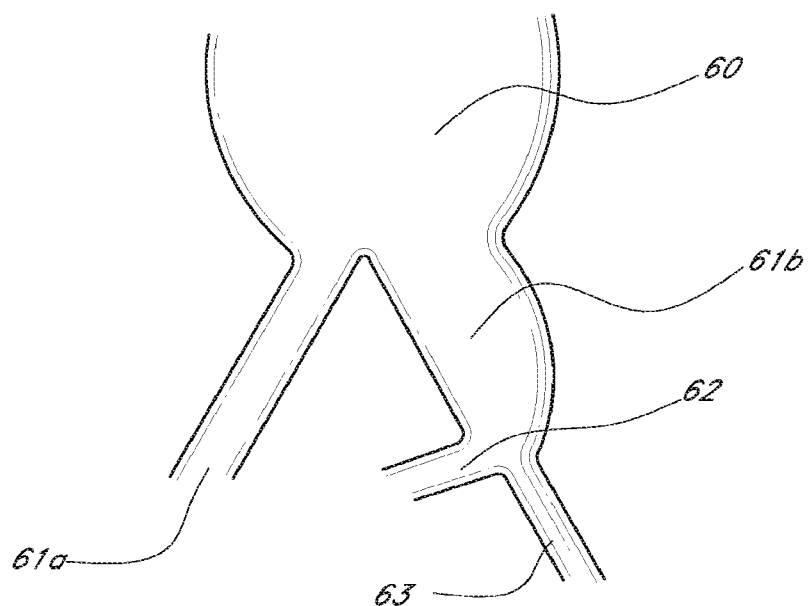
FIG. 11 illustrates an aneurysmal common iliac in an abdominal aortic aneurysm.

FIG. 11 shows an abdominal aneurysm with one diseased common iliac artery 61b. The common iliac artery 61b is enlarged. An enlarged common iliac artery may compromise the distal seal when stent grafting the aneurysm. Specifically blood may flow from the hypogastric artery 62 into the aneurysm sac 60, thereby pressurizing the sac.

Figure 12:
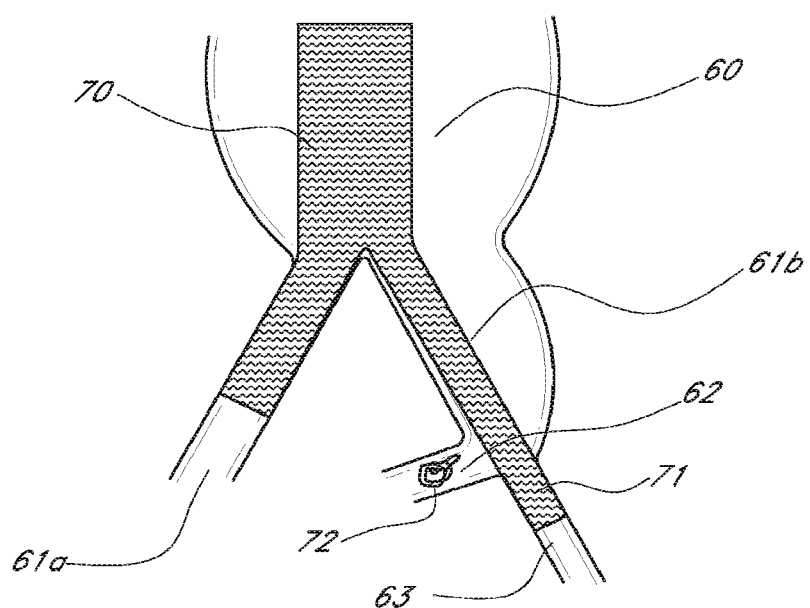
FIG. 12 illustrates an aneurysmal common iliac treated with an embodiment of a coiled member in the hypogastric artery and an embodiment of a stent graft into the external iliac artery.

FIG. 12 illustrates an aneurismal common iliac treated with an embodiment of a coiled member 72 in the hypogastric artery and an embodiment of a stent graft 70 into the external iliac artery. As such, FIG. 12 illustrates one strategy to stent graft an abdominal aneurysm with one diseased common iliac artery as shown in FIG. 11. First, in some embodiments, the hypogastric artery 62 can be embolized. This can be accomplished by placing the coiled member 72 in the hypogastric artery 62. Alternatively, an alternative form of a plug can be deployed in the hypogastric artery 62. After embolization of the hypogastric artery 62, in some embodiments, a stent graft 70 can be placed in the aneurysm 60, the stent graft 70 having an extended branch graft 71 that can extend into the external iliac artery 63 to provide a distal seal.

Figure 13:
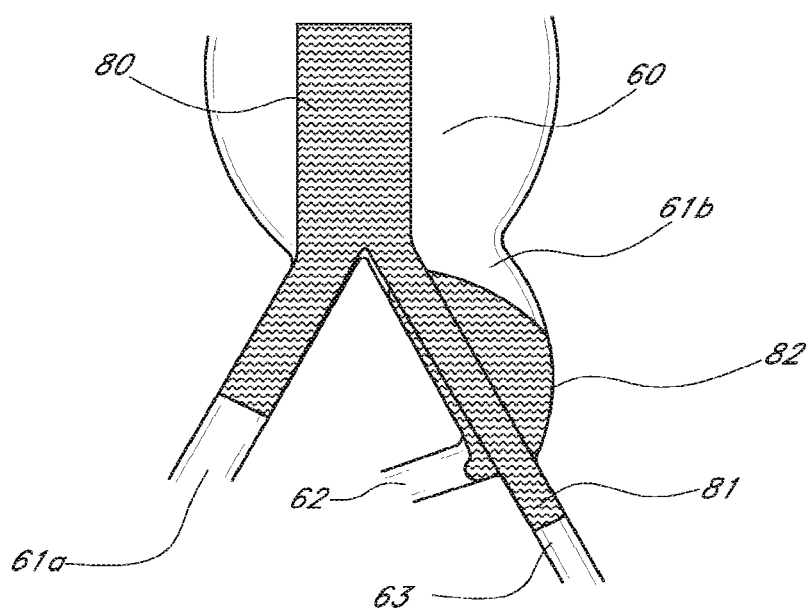
FIG. 13 illustrates an aneurismal common iliac treated with an embodiment of a bifurcated stent graft with a two-layer iliac stent graft segment.

FIG. 13 illustrates an alternative strategy for the endovascular treatment of the abdominal aneurysm with one diseased common iliac artery as shown in FIG. 11. The stent graft 80 can have a branch graft 81 with a two-layer graft cover described in FIG. 5. The arterial pressure can inflate the outer graft cover 82 and the outer graft 82 can cover and seal the hypogastric artery 62 and at least partially fill the diseased portion of the common iliac artery 61b. The concept can work similar to the occlusion of the lumbar arteries in the aneurysm sac. The proposed strategy can eliminate the need for coiling, which often has to be done in a separate procedure prior to stent grafting.

Figure 14:
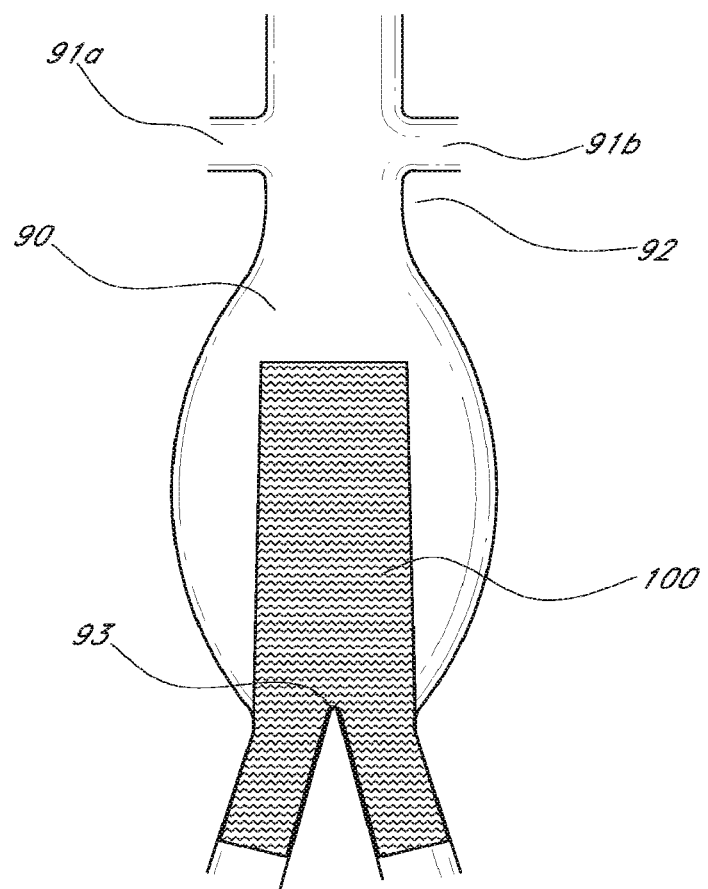
FIG. 14 illustrates an embodiment of a bifurcated stent graft to treat an abdominal aortic aneurysm with a short proximal neck.
Figure 15:
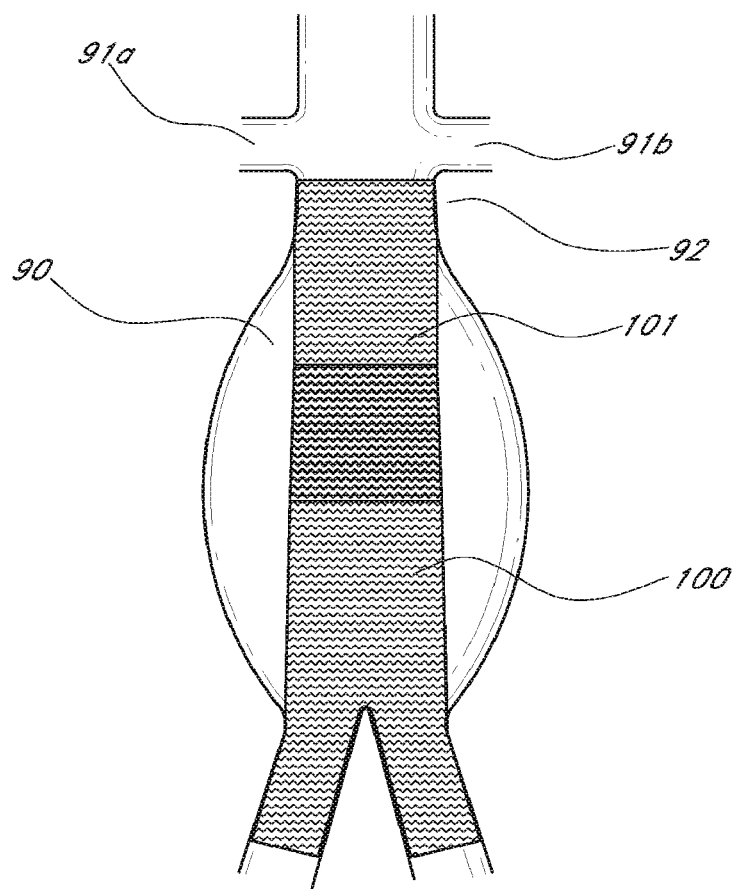
FIG. 15 illustrates an embodiment of a proximal extension placed in an embodiment of a bifurcated stent graft to treat an abdominal aortic aneurysm with a short proximal neck.
Figure 16:
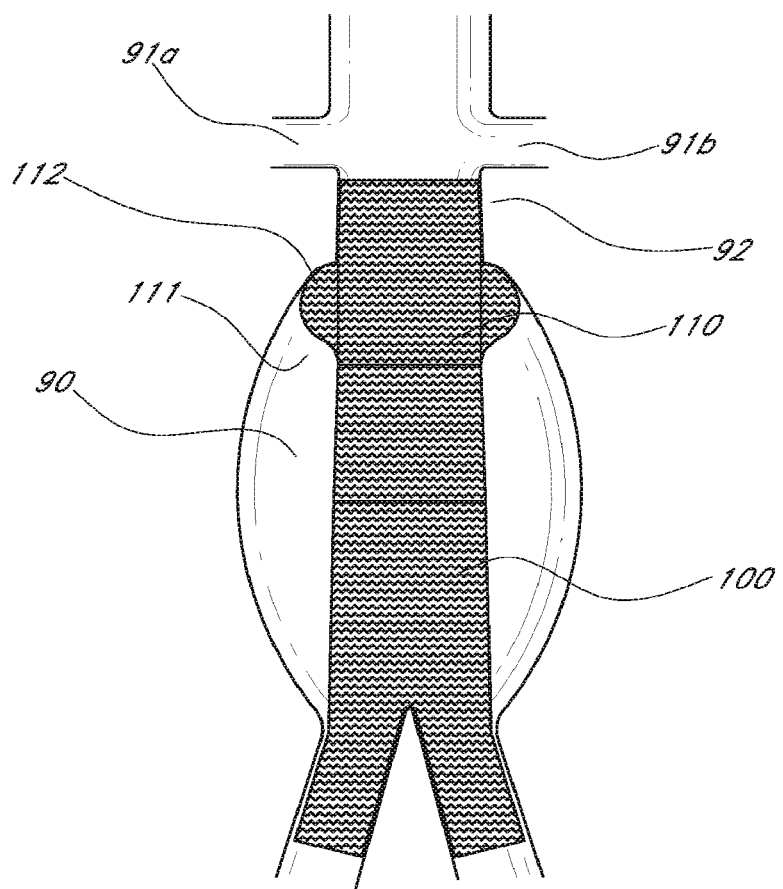
FIG. 16 illustrates another embodiment of a two-layer proximal extension placed in an embodiment of a bifurcated stent graft to treat an abdominal aortic aneurysm with a short proximal neck.

FIGS. 14-16 illustrate another application of the two-layer graft cover. FIG. 14 shows a bifurcated stent graft 100 placed onto the anatomical bifurcation 93 for stent grafting of an abdominal aortic aneurysm 90. The bifurcated device 100 can provide a platform for subsequent graft placement at the aortic neck 92. In FIG. 15, an embodiment of a tubular stent graft extension 101 can be placed to overlap with the bifurcated stent graft 100 and seal the aneurysm below the renal arteries 91a and 91b. Distance between the renal arteries and the aneurysm sac is often referred to as the proximal neck 92, and the distance between the proximal end of the stent graft 101 and the aneurysm sac 90 is often referred to as the proximal seal zone. It can be preferred to place the proximal end of the stent graft 101 right below the renal arteries 91a and 91b to maximize the length of the proximal seal zone. In short-neck aneurysms, the potential seal zone may be too short to provide an adequate seal. Commercially available stent graft systems typically require a neck length of at least 10-15 mm to ensure a proper proximal seal.

FIG. 16 shows an embodiment of a two-layer stent graft extension 110 placed in the proximal neck 92 of the aortic aneurysm 90. The inflated outer layer 111 can extend the contact length 112 between the stent graft 110 and the aortic wall into the aneurysm sac 90 effectively increasing the proximal seal zone.

Figure 17:
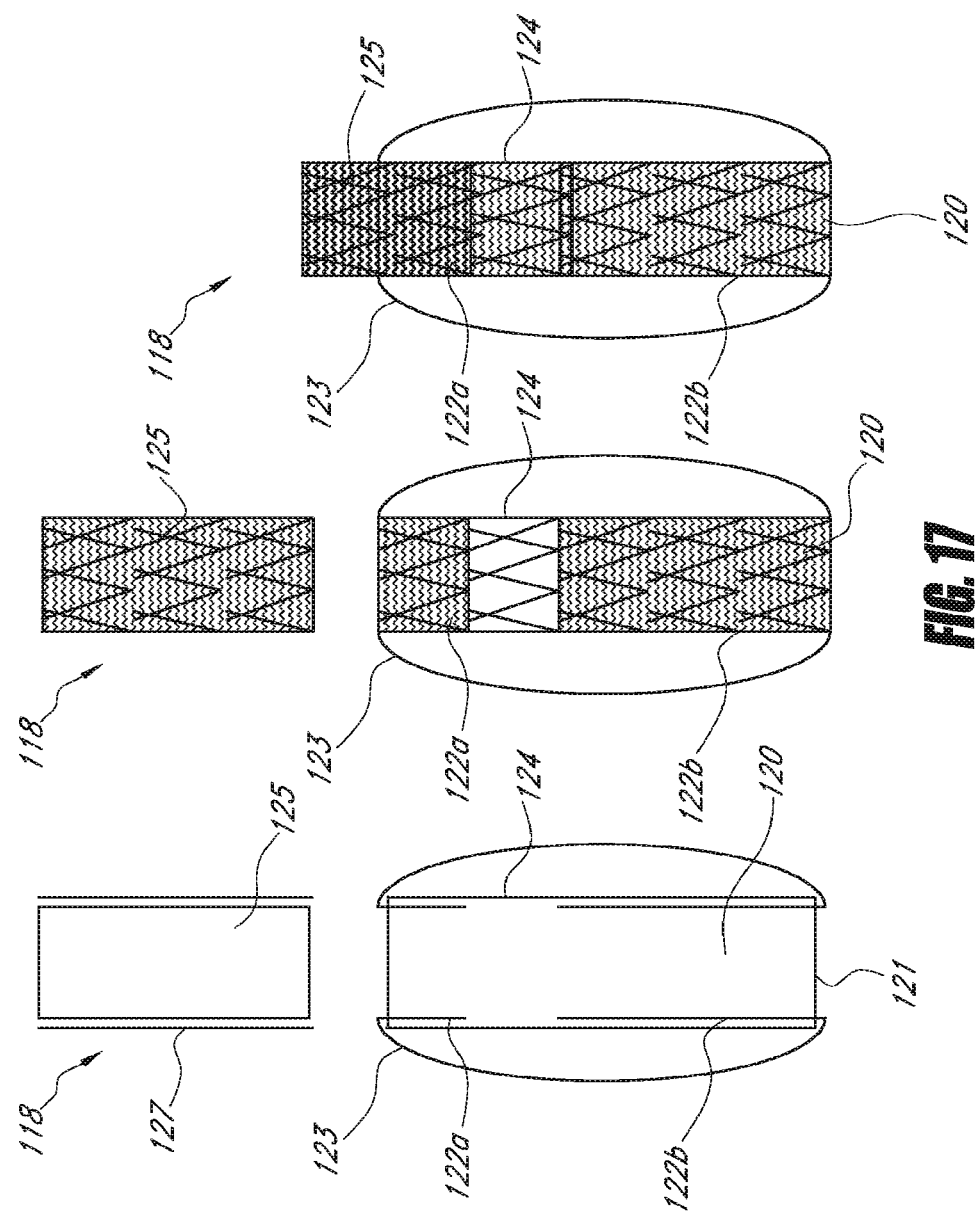
FIG. 17 illustrates another embodiment of a stent graft system comprising a first graft having two graft layers and a second graft acting as a sealing member.

FIG. 17 illustrates another embodiment of a stent graft system 118, which can be a two-layer stent graft system. The stent graft system can be tubular, bifurcated The graft system 118 can comprise a first stent graft 120, which can have a tubular stent graft 121 and one or more tubular inner graft or graft segments 122 that partially cover the stent 121. With reference to FIG. 17, some embodiments of the stent graft system 118 can have a first inner graft 122a and a second inner graft 122b that can be positioned adjacent to the end portions of the stent 121. In some embodiments, the first inner graft 122a and a second inner graft 122b can be spaced apart so that a portion of the stent 121 can be uncovered by the inner graft 122. For example, without limitation, a portion of the midsection 124 of the stent 121 can be uncovered. Either or both of the first inner graft 122a and a second inner graft 122b can be positioned on an inside surface of the stent 121 (as illustrated), or can be positioned on an outside surface of the stent 121.

An outer graft cover 123 can be connected to or otherwise supported by the stent 121 at one or both ends. The outer graft cover 123 can have a constant diameter, or can have a varying diameter along a length thereof. In some embodiments, the middle portion of the outer graft cover 123 can define a larger diameter than one or more of the end portions of the outer graft cover 123. In some embodiments, the diameter of some or all of the outer graft cover 123 can be greater than the diameter of the first inner graft 122a and/or second inner graft 122b. The uncovered midsection 124 can provide for rapid filling of the outer graft cover 123 with the patient's blood, as is illustrated in FIG. 17. A second stent graft 125 can be placed inside the first stent graft 120 to seal the space created between the outer graft cover 123 and the inner graft 122. The graft 127 of the second stent graft 125, the inner graft 122 and the outer graft 123 of the first stent graft 120 can form a sealed space in which the patient's blood can be trapped.

Figure 18:
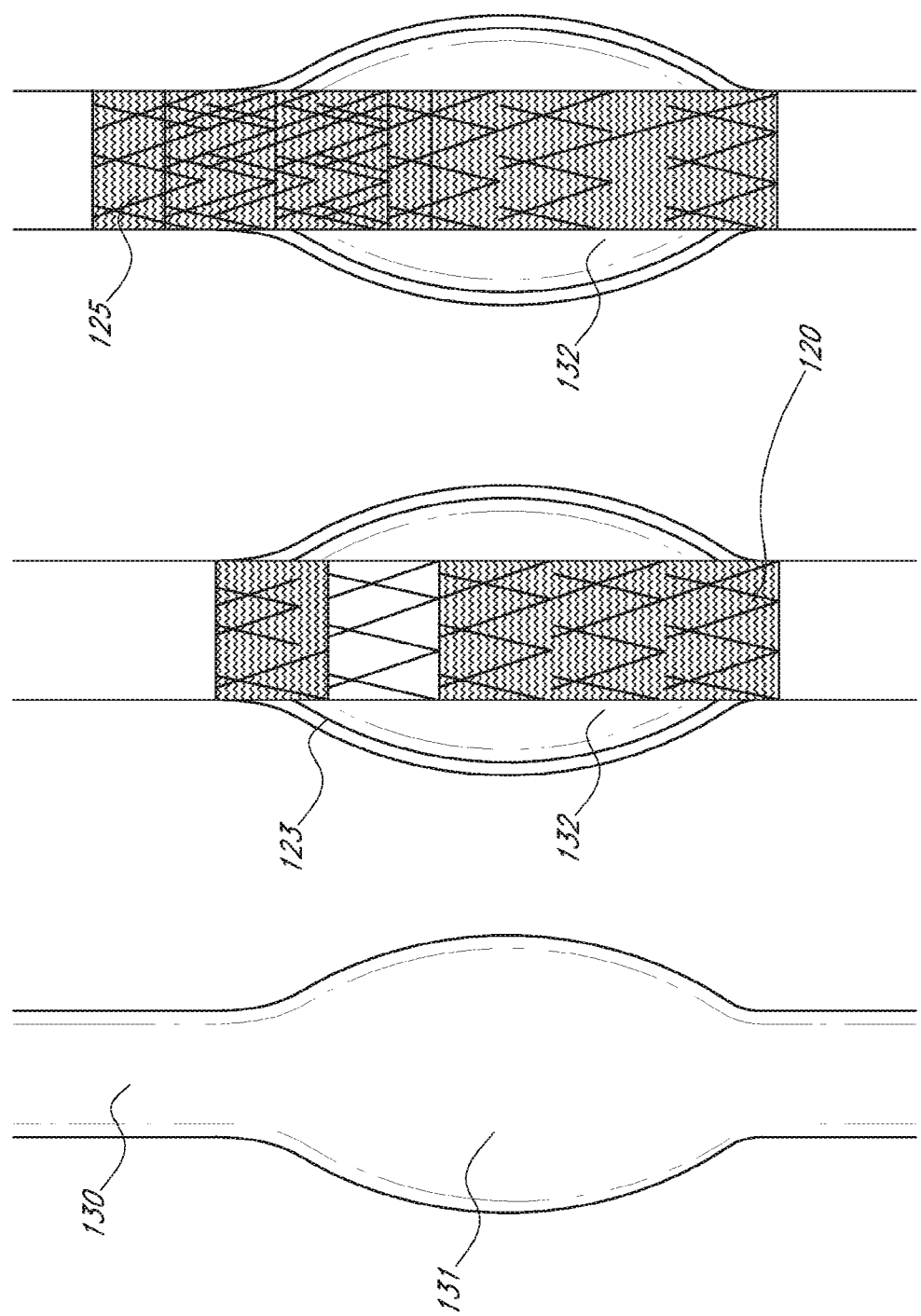
FIG. 18 illustrates the placement of the embodiment of the graft system from FIG. 17 into an aneurysm.

FIG. 18 illustrates the placement of the stent graft system 118 in an aneurysm 131 of the aorta 130. When the first stent graft 120 is placed over the aneurysm sac 131, the blood pressure in the aorta 130 can force blood into the space 132 and can inflate the outer graft cover 123. The second stent graft 125 can be placed inside the first stent graft 120 and can be configured to substantially or completely seal the space 132.

FIG. 19 illustrates another embodiment of a stent graft system 138. The first stent graft 140 can be a bifurcated stent graft for the treatment of aorto-iliac aneurysms. In some embodiments, the embodiment of the stent graft system 138 can have any of the same features, components, or other details of any of the other embodiments of stent graft systems disclosed herein. In some embodiments, the second stent graft 141 can be a straight tubular stent graft. One advantage of the system comprising two stent grafts is that the space inside the outer graft cover can fill rapidly. Apertures or other small openings in the inner graft cover may reduce the flow into the space. They may also clog or get obstructed by emboli and thrombus. Another advantage is that the second stent graft can provide an instantaneous seal. In case of apertures or small openings, blood exiting the sac during the coagulation phase may form emboli or thrombus. Another advantage is the ability to inject contrast medium into the space to verify inflation of the outer graft cover.

The concept of a second stent graft can also be applied to the embodiments described herein with regard to, without limitation, FIGS. 5, 13, and 15. The second stent graft can be placed to cover the segments of the first stent graft that contains the openings for the blood to enter into the outer graft layer.

Figure 20:
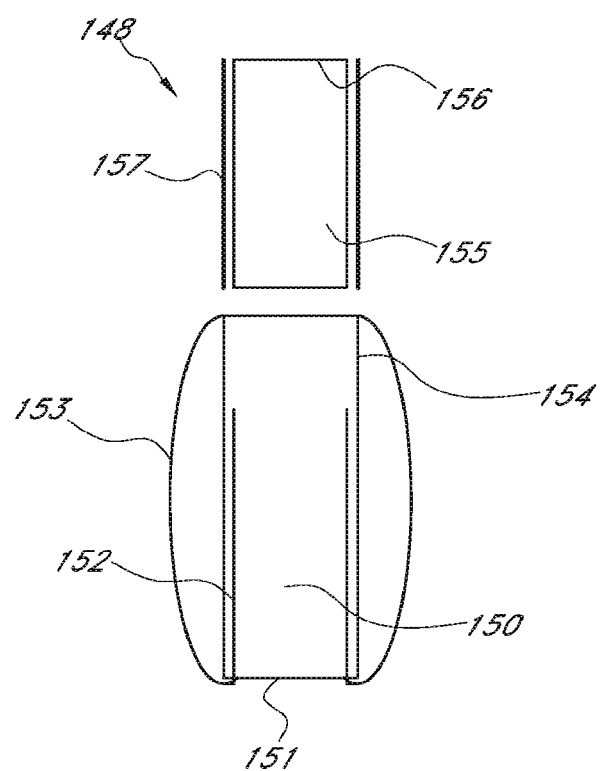
FIG. 20 illustrates another embodiment of a stent graft system.

FIG. 20 illustrates another embodiment of a stent graft system 148, which can be a two-layer stent graft system. In some embodiments, the stent graft system 148 can have any of the components, features, or other details of any of the other stent graft system embodiments disclosed herein, including without limitation the stent graft system 118 described above.

With reference to FIG. 20, the graft system 148 can comprise a first stent graft 150, which can have a tubular stent 151 and one or more tubular inner graft or graft segments 152 that partially cover the stent 151. A portion 154 of the stent 151 can be uncovered. In some embodiments, the uncovered portion 154 of the stent 151 can be located near an end portion of the stent 151. An outer graft cover 153 can be connected to or otherwise supported by the stent 151 at one or both ends. The uncovered portion 154 can provide for rapid filling of the outer graft cover 153 with the patient's blood. A second stent graft 155 can be placed inside the first stent graft 150 to seal the space created between the outer graft cover 153 and the inner graft 152. In some embodiments, the second stent graft 155 can be placed inside the first stent graft 150 after the outer graft cover 153 has been sufficiently filled with blood. The graft 157 of the second stent graft 155, the inner graft 152 and the outer graft 153 of the first stent graft 150 can form a sealed space in which the patient's blood can be trapped.

In some embodiments, the outer graft cover 153 can be placed on the outside of the stent 151 and inverted at the ends to partially cover the inside of the stent 152. The open stent segment 155 can be located close to one end of the stent graft system. In some embodiments, the outer graft cover 157 can be configured to only form a hem at one end of the stent 151.

FIG. 21A illustrates some of the components of another embodiment of a stent graft 180, showing the components in an unassembled state. FIG. 21B illustrates the embodiment of the stent graft 180 of FIG. 21A, showing the components in the assembled state. With reference to FIGS. 21A and 21B, the stent graft system 180 can have a graft 181 and a stent 182, and can have one or more flow valves therein configured to allow flow of fluid through said valves or openings in only one direction. The stent graft system 180, or any other stent graft system disclosed herein, can have a bifurcated stent graft (as illustrated), a tubular stent graft (not illustrated), or any other suitable configuration of a stent graft, such as curved, tapering, or otherwise.

The bifurcated graft 181 can have a main graft body portion 184, a first graft branch portion 185, and a second graft branch portion 186. Similarly, the stent 182 can have a main stent body portion 187, a first stent branch portion 188, and a second stent branch portion 189. The stent 182, or any other stent embodiment disclosed herein, can provide substantially continuous scaffolding along the length thereof, or can be formed in segments or discrete portions that can be interconnected directly to other stent segments portions or can be held in the desired position by attachment to the graft material. In some embodiments, the stent 182, or segments or portions thereof, can be sutured or otherwise attached to the graft 181. In some embodiments, as in the illustrated embodiment, the proximal portion 182*a* of the stent 182 can extend proximal to the proximal end 181*a* of the graft 181 so that such proximal portion 182*a* of the stent 182 is not covered by the graft 181.

One or more openings 190 can be formed in the graft 181. In the illustrated embodiment, one opening 190 is formed laterally through a side wall of the main graft body portion 184 of the graft 181. The opening 190 can be formed in any desired position of the graft 181. As illustrated, in some embodiments, the opening 190 can be positioned so that blood can flow through the one or more opening 190, similar to the openings 37 described above with reference to FIGS. 5 and 6. The opening or openings 190, or any other openings disclosed herein, can be positioned in the graft 181 so as to be positioned between the struts, wires, or other members of the stent which the graft covers.

With reference to FIG. 21A, the stent graft system 180, or any other stent graft system disclosed herein, can have a second graft member 200 having a tabbed or flap portion 202 (also referred to herein as a flap member, valve cover, or just cover). As will be discussed in greater detail, the openings 190 and covers 202 can form single directional flow valves to permit flow into the space surrounding the graft 184 and second graft member 200. The second graft member 200 can have a tubular shape and can be configured to surround at least a portion of the length of the stent 182 around all or a portion of the circumference of the stent 182. As illustrated in FIG. 21B, the second graft member 200 can be configured to be positioned over the outside surface of the proximal portion 182*a* of the stent 182, and can be sized and configured so that the tabbed portion 202 can cover the opening 190. In some embodiments, the second graft member 200 can be sutured or otherwise attached to the graft 181. For example, without limitation, the second graft member 200 can be fixed to the graft 181 using one or more sutures 206 circumferentially positioned around the stent graft system 180, as illustrated in FIG. 21B.

In some embodiments, the flap member 202 can be formed on or affixed to the main graft body portion 184 of the graft 181. Without limitation, the flap member 202 can cover a portion of the length of the stent 182 and all or a portion of the circumference of the stent 182. In some arrangements, the flap member 202 can be stitched, sutured, adhered, or otherwise attached to the outside surface of the main graft body portion 184 of the graft 181.

An outer graft member 212 can be positioned over an outside surface of the main graft body portion 184 and the second graft member 200. The outer graft member 212 can be sealingly fixed to the main graft body portion 184 and the second graft member 200 so that a substantially sealed space 214 is created between the outer graft member 212 and the main graft body portion 184 and/or the second graft member 200. The stent graft system 180 can be configured so that blood can pass from the inside of the main graft body 184 through the opening 190 and into the space 210 formed inside the outer graft member 212, but so that the tabbed portion 202 inhibits or substantially prevents blood from flowing from the space 214 back through the opening 190.

In this arrangement, similar to other embodiments described above, blood in the aorta can pass through the openings 190 into the space 214 formed inside the outer graft member 212, causing the outer graft cover 212 to inflate until it substantially fills or approximately completely fills an aneurysm sac. The blood in the space 214 can ultimately coagulate and form a thrombus.

The graft 181, second graft member 200, the outer graft member 212, or any other graft embodiment disclosed herein can be formed from PTFE, ePTFE, or any other suitable material. The stent 182, or any other stent embodiment disclosed herein, can be formed from Nitinol, stainless steel, a shape memory or heat activated material, or any other suitable material. The stent 182, or any other stent embodiment disclosed herein, can be self-expandable, balloon expandable, or expandable by any other mechanical or other means such as, without limitation, heat.

FIG. 22A illustrates some of the components of another embodiment of a stent graft 180', showing the components in an unassembled state. FIG. 22B illustrates the embodiment of the stent graft 180' of FIG. 22A, showing the components in the assembled state. With reference to FIGS. 22A and 22B, the stent graft system 180' can have a graft 181' and a stent 182. The stent graft system 180' can have any of the same features, configurations, or other details of the stent graft system 180 described above, except as described below.

With reference to FIGS. 22A, 22B, the main graft body portion 184' of the graft 181' can have two or more openings 190' formed therein (two openings 190' being illustrated). Additionally, the second graft member 200' can have a tabbed or flap portion 202' that can be configured to cover each of the two or more openings 190'. Although not required, in some embodiments, the tabbed portion 202' can have a slit 203' between the portions of the tabbed portion 202' that cover each of the openings 190'.

Figure 23B:
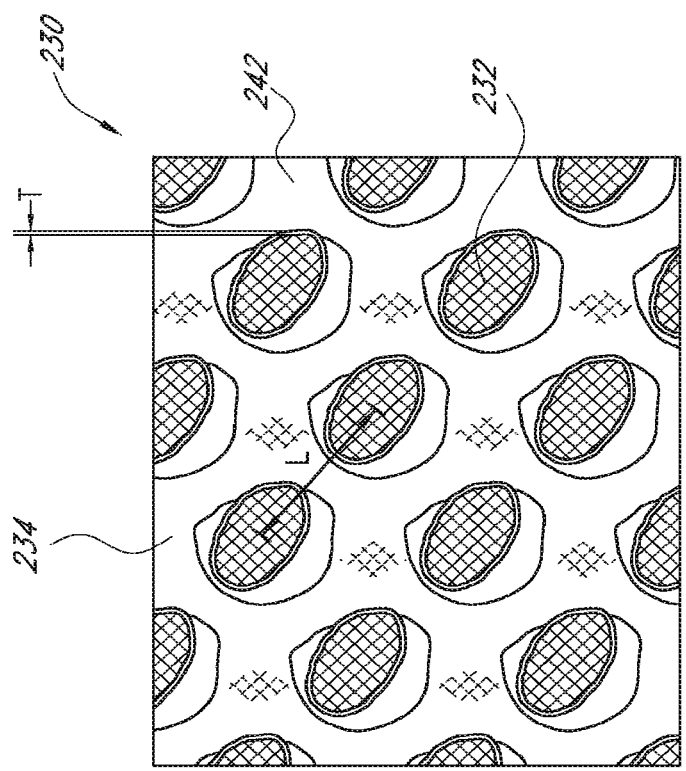
FIG. 23B is a top view of a portion of the layer or layers comprising the embodiment of a porous or perforated inner graft of FIG. 23A.
Figure 23A:
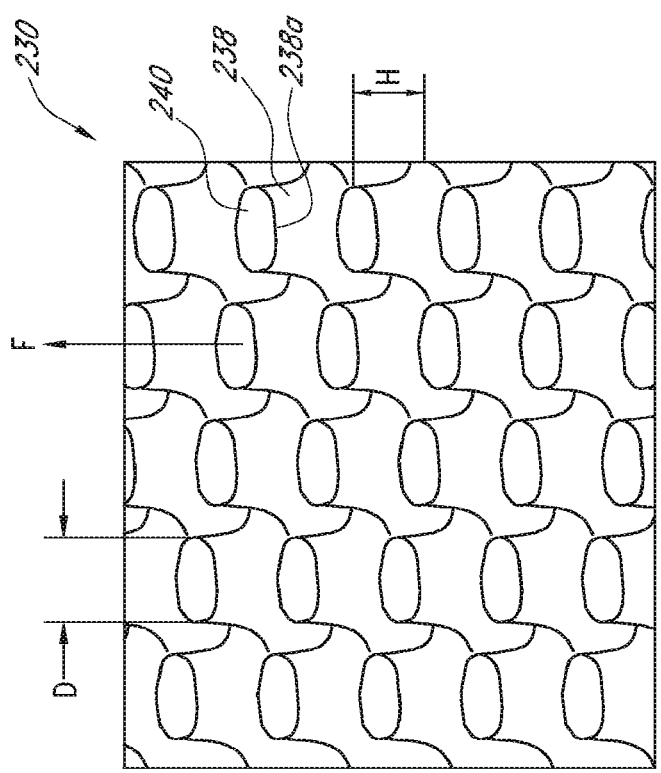
FIG. 23A is a perspective view of a portion of the layer or layers comprising an embodiment of a porous or perforated inner graft.

FIG. 23A is a perspective view of a portion of the layer or layers comprising an embodiment of a porous or perforated inner graft 230. FIG. 23B is a top view of a portion of the layer or layers comprising the embodiment of a porous or perforated inner graft 230 of FIG. 23A. In some embodiments, with reference to FIGS. 23A, 23B, the inner graft 230 can have a base layer 232 and an outer layer 234 and one or more flow direction valve members, as will be described in greater detail. In some embodiments, the base layer 232 can be porous or otherwise pervious, or can be impervious and define a plurality of openings therethrough. The base layer 232 can be made from PTFE, ePTFE, polyester, or any other suitable material, and can be woven, wrapped or otherwise formed from a sheet, or otherwise. In some embodiments, the base layer 232 can be substantially impervious, and the tubules 238 and openings 240 can be formed directly in the base layer 232.

The outer layer 234 can be formed from a substantially or completely impervious material having one or more channels or tubules 238 projecting away from the base layer, the tubules 238 each having an opening 240 in a distal end 238*a* thereof. The tubules 238 can be formed from a thin cylinder or cone of material so that the walls of said tubules 238 are tapered. The tubules 238 can be configured to permit fluid flow therethrough in only one direction (for example, in the direction indicated by arrow "F" in FIG. 23A), and can be configured to prevent or substantially inhibit the flow of fluid (such as blood) in the opposite direction. For example, as discussed above, the tubules 238 can be formed on an outside surface of any embodiments of the inner graft disclosed herein so as to project outwardly away from the outside surface of the inner graft 230. In some embodiments, the outer layer 234 can cover substantially all of the porous or pervious base layer 232 so that substantially the entire inner graft 230 comprises one-way flow control.

The tubules 238 can have a thickness (represented by "T" in FIG. 23B), opening diameter or size (represented by "D" in FIG. 23A), and height (represented by "H" in FIG. 23B) configured such that the tubules 238 collapse or otherwise substantially close when a fluid pressure acting against an outside surface 242 of the inner graft 230 is greater than a fluid pressure acting against an opposite, inside surface of the inner graft. The material chosen for the film or outer layer 232 (or the inner layer 234 if the tubules 238 are formed therein) can affect the optimal thickness T, diameter D, and/or height H of the tubules 238.

In some embodiments, the diameter or size D of the openings 240 can range from approximately 20 μm or less to 2 mm or more, and can have a height H from approximately one half of the diameter D to 5 times the diameter D, and a thickness T from approximately 2 μm or less to approximately 100 μm or more. Further, depending on the desired flow rate through the inner graft 230 and number of tubules 238 formed in the inner graft 230, the tubules 238 can be spaced apart by distance "L" shown in FIG. 23B that can range from approximately 120 μm or less to approximately 5 mm or more.

Thrombosis of the blood in the space between the inner graft cover and the outer graft cover can stop or significantly reduce the communication of the pressure in the flow lumen to the vessel wall. The blood in the space can coagulate and thrombose once the blood is stagnant. The coagulation process can be accelerated by placing a thrombotic agent into the space between the inner and outer graft cover. Suitable agents can include, but are not limited to, salts, silk, albumin, and fibrin. The agents can be placed in the space in powder form or coating of the inner surfaces of the inner and outer graft cover. The opening into the space can be treated with a thrombotic agent to seal off the opening after the outer graft cover has been inflated. For example, a section of the inner graft cover can be made from a woven or knitted porous silk fabric.

Although the inventions have been disclosed in the context of a preferred embodiments and examples, it will be understood by those skilled in the art that the present disclosure extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It can be also contemplated that various combinations or subcombinations of the specific features and aspects of the embodiments can be made and still fall within the scope of the invention. Accordingly, it should be understood that various features and aspects of the disclosed embodiments can be combine with or substituted for one another in order to form varying modes of the disclosed invention. Thus, it can be intended that the scope of the present disclosure herein disclosed should not be limited by the particular disclosed embodiments described above.

What is claimed is:

1. A stent graft, comprising:
   a main body;
   branch grafts that extend from an end of the main body;
   an inner graft cover; and
   an outer graft cover that covers at least a portion of the inner graft cover and that is completely uncovered by the branch grafts;
   wherein the inner graft cover is made of a blood-impermeable non-porous material perforated to have one or more openings formed by punching therein to allow fluid communication of blood between an inner lumen of the main body and a space between the inner graft cover and the outer graft cover.

2. The stent graft of claim 1, wherein the outer graft cover is made from a same material as the inner graft cover.

3. The stent graft of claim 1, wherein the outer graft cover has one or more radiopaque markers thereon to provide visualization of a position or level of inflation of the outer graft cover during deployment.

4. The stent graft of claim 1, wherein a diameter of the outer graft cover is larger than a diameter of the inner graft cover.

5. The stent graft of claim 1, wherein the inner graft cover and the outer graft cover are connected at distal and proximal ends to form the space between the inner graft cover and the outer graft cover.

6. The stent graft of claim 1, wherein each of the one or more openings in the inner graft cover are large enough to allow blood cells to enter the space between the inner graft cover and the outer graft cover from the lumen of the main body.

7. The stent graft of claim 6, wherein each of the one or more openings in the inner graft cover are small enough to prevent flow patterns to form in the space that would delay blood coagulation.

8. The stent graft of claim 1, wherein each of the one or more openings in the inner graft cover has a length of between 20 μm and 5 mm.

9. The stent graft of claim 1, wherein each of the one or more openings in the inner graft cover has a length of between 100 μm and 2 mm.

10. The stent graft of claim 1, wherein the one or more openings in the inner graft cover include two or more openings in the inner graft cover.

11. The stent graft of claim 1, wherein the one or more openings in the inner graft cover are one or more holes in a graft material of the inner graft cover.

12. The stent graft of claim 1, wherein the one or more openings in the inner graft cover are configured to only allow one directional fluid flow.

13. The stent graft of claim 1, wherein the one or more openings in the inner graft cover are configured to permit fluid to flow from the inner lumen of the main body to the space between the inner graft cover and the outer graft cover and to prevent the flow of fluid from flowing in an opposite direction.

14. The stent graft of claim 1, wherein the outer graft cover is configured to only cover a portion of the inner graft cover.

15. The stent graft of claim 1, wherein the outer graft cover is configured to only cover a distal portion of the inner graft cover.

16. The stent graft of claim 1, wherein the outer graft cover is configured to only cover a proximal portion of the inner graft cover.

17. The stent graft of claim 1, wherein the outer graft cover is configured to only cover a mid-section of the inner graft cover.

18. A stent graft, comprising:
a main body;
branch grafts that extend from an end of the main body;
an inner graft cover; and
an outer graft cover that covers at least a portion of the inner graft cover and that is completely uncovered by the branch grafts;
wherein the inner graft is made from a non-porous material comprising at least two circumferentially aligned openings, said openings configured to allow fluid communication of blood between an inner lumen of the main body and a space between the inner graft cover and the outer graft cover.

19. The stent graft of claim 18, wherein the non-porous material is blood impermeable.

* * * * *